(12) United States Patent
Brennan et al.

(10) Patent No.: US 8,431,532 B2
(45) Date of Patent: Apr. 30, 2013

(54) FZD8 EXTRACELLULAR DOMAINS AND FZD8 EXTRACELLULAR DOMAIN FUSION MOLECULES AND TREATMENTS USING SAME

(75) Inventors: Thomas Brennan, San Jose, CA (US); Ernestine Lee, Kensington, CA (US); Steven Smith, San Francisco, CA (US)

(73) Assignee: Five Prime Therepeutics, Inc., South San Francisco, CA (US)

( * ) Notice: Subject to any disclaimer, the term of this patent is extended or adjusted under 35 U.S.C. 154(b) by 0 days.

(21) Appl. No.: 13/169,900

(22) Filed: Jun. 27, 2011

(65) Prior Publication Data

US 2012/0003222 A1 Jan. 5, 2012

Related U.S. Application Data

(60) Provisional application No. 61/359,214, filed on Jun. 28, 2010.

(51) Int. Cl.
*A61K 38/17* (2006.01)

(52) U.S. Cl.
USPC ............... 514/6.8; 514/5.2; 514/7.4; 514/4.8; 514/4.9; 514/21.2; 514/15.2; 424/178.1; 530/402; 530/362

(58) Field of Classification Search .................. None
See application file for complete search history.

(56) References Cited

U.S. PATENT DOCUMENTS

| | | | |
|---|---|---|---|
| 6,686,179 B2 | 2/2004 | Fleer et al. | |
| 6,900,292 B2 | 5/2005 | Sun et al. | |
| 7,541,431 B2 * | 6/2009 | Yoon | |
| 7,723,477 B2 | 5/2010 | Gurney et al. | |
| 7,947,277 B2 | 5/2011 | Ernst et al. | |
| 8,183,207 B2 * | 5/2012 | Lin et al. | |
| 2002/0137129 A1 | 9/2002 | Barnes et al. | |
| 2003/0165500 A1 | 9/2003 | Rhee et al. | |
| 2004/0247593 A1 | 12/2004 | He et al. | |
| 2006/0019256 A1 | 1/2006 | Clarke et al. | |
| 2006/0019320 A1 | 1/2006 | Civenni et al. | |
| 2007/0116701 A1 | 5/2007 | Gurney et al. | |
| 2010/0104574 A1 | 4/2010 | Gurney et al. | |
| 2011/0305695 A1 * | 12/2011 | Satyal et al. | |

FOREIGN PATENT DOCUMENTS

| | | |
|---|---|---|
| WO | 2006/076288 | 7/2006 |
| WO | 2006/081430 | 8/2006 |
| WO | 2006130076 A1 | 12/2006 |

(Continued)

OTHER PUBLICATIONS

Momoi et al., Analysis of Wnt8 for neural posteriorizing factor by identifying Frizzled 8c and Frizzled 9 as functional receptors for Wnt8, Mech. Dev. 120:477-489, 2003.*

(Continued)

*Primary Examiner* — Claire Kaufman
(74) *Attorney, Agent, or Firm* — Casimir Jones, S.C.

(57) ABSTRACT

Methods of treatment using Fzd8 extracellular domains (ECDs), Fzd8 ECD fusion molecules, and/or antibodies that bind Fzd8 are provided. Such methods include, but are not limited to, methods of treating obesity and obesity-related conditions. Fzd8 ECDs and Fzd8 ECD fusion molecules are also provided. Polypeptide and polynucleotide sequences, vectors, host cells, and compositions comprising or encoding such molecules are provided. Methods of making and using Fzd8 ECDs, Fzd8 ECD fusion molecules, and antibodies that bind Fzd8 are also provided.

11 Claims, 14 Drawing Sheets

FOREIGN PATENT DOCUMENTS

| WO | 2007/053577 | 5/2007 |
|---|---|---|
| WO | 2007/133250 | 11/2007 |
| WO | 2008031009 A2 | 3/2008 |
| WO | 2010/037041 | 4/2010 |

OTHER PUBLICATIONS

Kanasaki et al., Biology of Obesity:Lessons from animal models of obesity, J. Biomedicine Biotech. 2011, article ID 197636, 11 pages, 2011, retrieved online on May 31, 2012, at [http://www.hindawi.com/journals/jbb/].*

StemRD, Frizzled-8 Fc fusion, human product sheet, Cat. #HFZ8FC, 2009 [retrieved online on Jun. 1, 2012]. Retrieved from the internet: <URL:http://stemrd.com/index.php?/WNT-pathway/Frizzled-8-Fc-fusion-human/flypage.tpl.htm>].*

Higuchi, H., Neuropeptide Y, Folia Pharmacol. Japon. 93:203-218, 1989.*

Bennett, C. et al., Role of Wnt10b and C/EBPalpha in spontaneous adipogenesis of 243 cells, Biochem. Biophys, Res. Comm. (2003) 302:12-16.

Chen, Z. et al., Improved Production and Purification of Minicircle DNA Vector Free of Plasmid Bacterial Sequences and Capable of Persistent Transgene Expression In Vivo, Hum. Gene Ther. (2005) 16:126-131.

Choo, K. et al., SPdb—a signal peptide database: BMC Bioinfor. (2005) 6:249.

Christodoulides, C. et al., The Wnt antagonist Dickkopf-1 and its receptors are coordinately regulated during early human adipogenesis, J. Cell Sci. (2006) 119:2613-2620.

Harris, M., Obesity Treatment and Trends, Today and Tomorrow, BioWorld Today (2010) 6-10.

Kanazawa, A. et al., Wnt5b partially inhibits canonical Wnt/beta-catenin signaling pathway and promotes adipogenesis in 3T3-L1 preadipocytes, Biochem. Biophys Res. Comm. (2005) 330:505-510.

Okada, Y. et al., Diet-Induced Up-Regulation of Gene Expression in Adipocytes Without Changes in DNA Methylation, Kobe J. Med. Sci. (2008) 54(5):E241-E249.

Running Deer, J. et al., High-Level Expression of Proteins in Mammalian Cells Using Transcription Regulatory Sequences from the Chinese Hamster EF-1alpha Gene, Biotechnol. Prog. (2004) 20:880-889.

Dealmeida et al., "The Soluble Wnt Receptor Frizzled8CRD-hFc Inhibits the Growth of Teratocarcinomas In vivo," Cancer Res, 2007, 67:5371-5379.

Dann et al., "Insights into Wnt binding and signalling from the structures of two Frizzled cysteine-rich domains," Nature, 2000, 412:86-90.

Hu et al., "Tissue Restricted Expression of Two Human Frzbs in Preadiopocytes and Pancreas," Biochem Biophys Res Comm, 1998, 247:287-293.

Kim et al., "Comparative analysis of the secretory proteome of human adipose stromal vascular fraction cells during adipogenesis," pROTEOMICS, 2010, 0:394-405.

International Search Report and Written Opinion, mailed Oct. 31, 2011, for International Patent Application PCT/US2011/042033, 15 pages.

International Preliminary Report on Patentability, mailed Jan. 10, 2013, for International Patent Application PCT/US2011/042033, 9 pages.

* cited by examiner

SEQUENCE LISTING

<160> NUMBER OF SEQ ID NOS: 18

<210> SEQ ID NO 1
<211> LENGTH: 694
<212> TYPE: PRT
<213> ORGANISM: Homo sapiens
<220> FEATURE:
<221> NAME/KEY: misc_feature
<222> LOCATION: (1)..(694)
<223> OTHER INFORMATION: Human Fzd8 (with signal peptide)

<400> SEQUENCE: 1

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Ala Ala
145                 150                 155                 160

-continued

```
Pro Ser Pro Pro Arg Leu Pro Pro Pro Pro Gly Glu Gln Pro
            165                 170                 175

Pro Ser Gly Ser Gly His Gly Arg Pro Pro Gly Ala Arg Pro Pro His
        180                 185                 190

Arg Gly Gly Gly Arg Gly Gly Gly Gly Asp Ala Ala Ala Pro Pro
        195                 200                 205

Ala Arg Gly Gly Gly Gly Gly Gly Lys Ala Arg Pro Pro Gly Gly Gly
210                 215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255

Ile Ala Asn Cys Ala Leu Pro Cys His Asn Pro Phe Phe Ser Gln Asp
            260                 265                 270

Glu Arg Ala Phe Thr Val Phe Trp Ile Gly Leu Trp Ser Val Leu Cys
        275                 280                 285

Phe Val Ser Thr Phe Ala Thr Val Ser Thr Phe Leu Ile Asp Met Glu
    290                 295                 300

Arg Phe Lys Tyr Pro Glu Arg Pro Ile Ile Phe Leu Ser Ala Cys Tyr
305                 310                 315                 320

Leu Phe Val Ser Val Gly Tyr Leu Val Arg Leu Val Ala Gly His Glu
                325                 330                 335

Lys Val Ala Cys Ser Gly Gly Ala Pro Gly Ala Gly Gly Ala Gly Gly
            340                 345                 350

Ala Gly Gly Ala Ala Gly Ala Gly Ala Gly Ala Gly Ala Gly Ala Gly
        355                 360                 365

Gly Pro Gly Gly Arg Gly Glu Tyr Glu Glu Leu Gly Ala Val Glu Gln
    370                 375                 380

His Val Arg Tyr Glu Thr Thr Gly Pro Ala Leu Cys Thr Val Val Phe
385                 390                 395                 400

Leu Leu Val Tyr Phe Phe Gly Met Ala Ser Ser Ile Trp Trp Val Ile
                405                 410                 415

Leu Ser Leu Thr Trp Phe Leu Ala Ala Gly Met Lys Trp Gly Asn Glu
            420                 425                 430

Ala Ile Ala Gly Tyr Ser Gln Tyr Phe His Leu Ala Ala Trp Leu Val
        435                 440                 445

Pro Ser Val Lys Ser Ile Ala Val Leu Ala Leu Ser Ser Val Asp Gly
    450                 455                 460

Asp Pro Val Ala Gly Ile Cys Tyr Val Gly Asn Gln Ser Leu Asp Asn
465                 470                 475                 480

Leu Arg Gly Phe Val Leu Ala Pro Leu Val Ile Tyr Leu Phe Ile Gly
                485                 490                 495

Thr Met Phe Leu Leu Ala Gly Phe Val Ser Leu Phe Arg Ile Arg Ser
            500                 505                 510

Val Ile Lys Gln Gln Asp Gly Pro Thr Lys Thr His Lys Leu Glu Lys
        515                 520                 525

Leu Met Ile Arg Leu Gly Leu Phe Thr Val Leu Tyr Thr Val Pro Ala
    530                 535                 540

Ala Val Val Val Ala Cys Leu Phe Tyr Glu Gln His Asn Arg Pro Arg
545                 550                 555                 560

Trp Glu Ala Thr His Asn Cys Pro Cys Leu Arg Asp Leu Gln Pro Asp
                565                 570                 575

Gln Ala Arg Arg Pro Asp Tyr Ala Val Phe Met Leu Lys Tyr Phe Met
            580                 585                 590
```

```
Cys Leu Val Val Gly Ile Thr Ser Gly Val Trp Val Trp Ser Gly Lys
            595                 600                 605
Thr Leu Glu Ser Trp Arg Ser Leu Cys Thr Arg Cys Cys Trp Ala Ser
            610                 615                 620
Lys Gly Ala Ala Val Gly Gly Ala Gly Ala Thr Ala Ala Gly Gly
625                 630                 635                 640
Gly Gly Gly Pro Gly Gly Gly Gly Gly Pro Gly Gly Gly
            645                 650                 655
Gly Pro Gly Gly Gly Gly Ser Leu Tyr Ser Asp Val Ser Thr Gly
            660                 665                 670
Leu Thr Trp Arg Ser Gly Thr Ala Ser Ser Val Ser Tyr Pro Lys Gln
            675                 680                 685
Met Pro Leu Ser Gln Val
            690

<210> SEQ ID NO 2
<211> LENGTH: 667
<212> TYPE: PRT
<213> ORGANISM: Homo sapiens
<220> FEATURE:
<221> NAME/KEY: misc_feature
<222> LOCATION: (1)..(667)
<223> OTHER INFORMATION: Human Fzd8 (without signal peptide)

<400> SEQUENCE: 2

Ala Ser Ala Lys Glu Leu Ala Cys Gln Glu Ile Thr Val Pro Leu Cys
1               5                   10                  15
Lys Gly Ile Gly Tyr Asn Tyr Thr Tyr Met Pro Asn Gln Phe Asn His
            20                  25                  30
Asp Thr Gln Asp Glu Ala Gly Leu Glu Val His Gln Phe Trp Pro Leu
        35                  40                  45
Val Glu Ile Gln Cys Ser Pro Asp Leu Lys Phe Phe Leu Cys Ser Met
    50                  55                  60
Tyr Thr Pro Ile Cys Leu Glu Asp Tyr Lys Lys Pro Leu Pro Pro Cys
65                  70                  75                  80
Arg Ser Val Cys Glu Arg Ala Lys Ala Gly Cys Ala Pro Leu Met Arg
                85                  90                  95
Gln Tyr Gly Phe Ala Trp Pro Asp Arg Met Arg Cys Asp Arg Leu Pro
            100                 105                 110
Glu Gln Gly Asn Pro Asp Thr Leu Cys Met Asp Tyr Asn Arg Thr Asp
        115                 120                 125
Leu Thr Thr Ala Ala Pro Ser Pro Pro Arg Arg Leu Pro Pro Pro Pro
    130                 135                 140
Pro Gly Glu Gln Pro Pro Ser Gly Ser Gly His Gly Arg Pro Pro Gly
145                 150                 155                 160
Ala Arg Pro Pro His Arg Gly Gly Gly Arg Gly Gly Gly Gly Asp
                165                 170                 175
Ala Ala Ala Pro Pro Ala Arg Gly Gly Gly Gly Gly Lys Ala Arg
            180                 185                 190
Pro Pro Gly Gly Gly Ala Ala Pro Cys Glu Pro Gly Cys Gln Cys Arg
        195                 200                 205
Ala Pro Met Val Ser Val Ser Ser Glu Arg His Pro Leu Tyr Asn Arg
    210                 215                 220
Val Lys Thr Gly Gln Ile Ala Asn Cys Ala Leu Pro Cys His Asn Pro
225                 230                 235                 240
Phe Phe Ser Gln Asp Glu Arg Ala Phe Thr Val Phe Trp Ile Gly Leu
```

```
                    245                 250                 255
Trp Ser Val Leu Cys Phe Val Ser Thr Phe Ala Thr Val Ser Thr Phe
                260                 265                 270

Leu Ile Asp Met Glu Arg Phe Lys Tyr Pro Glu Arg Pro Ile Ile Phe
            275                 280                 285

Leu Ser Ala Cys Tyr Leu Phe Val Ser Val Gly Tyr Leu Val Arg Leu
        290                 295                 300

Val Ala Gly His Glu Lys Val Ala Cys Ser Gly Ala Pro Gly Ala
305                 310                 315                 320

Gly Gly Ala Gly Gly Ala Gly Gly Ala Ala Gly Ala Gly Ala Ala
                325                 330                 335

Gly Ala Gly Ala Gly Gly Pro Gly Gly Arg Gly Glu Tyr Glu Glu Leu
                340                 345                 350

Gly Ala Val Glu Gln His Val Arg Tyr Glu Thr Thr Gly Pro Ala Leu
            355                 360                 365

Cys Thr Val Val Phe Leu Leu Val Tyr Phe Gly Met Ala Ser Ser
    370                 375                 380

Ile Trp Trp Val Ile Leu Ser Leu Thr Trp Phe Leu Ala Ala Gly Met
385                 390                 395                 400

Lys Trp Gly Asn Glu Ala Ile Ala Gly Tyr Ser Gln Tyr Phe His Leu
                405                 410                 415

Ala Ala Trp Leu Val Pro Ser Val Lys Ser Ile Ala Val Leu Ala Leu
            420                 425                 430

Ser Ser Val Asp Gly Asp Pro Val Ala Gly Ile Cys Tyr Val Gly Asn
        435                 440                 445

Gln Ser Leu Asp Asn Leu Arg Gly Phe Val Leu Ala Pro Leu Val Ile
    450                 455                 460

Tyr Leu Phe Ile Gly Thr Met Phe Leu Leu Ala Gly Phe Val Ser Leu
465                 470                 475                 480

Phe Arg Ile Arg Ser Val Ile Lys Gln Gln Asp Gly Pro Thr Lys Thr
                485                 490                 495

His Lys Leu Glu Lys Leu Met Ile Arg Leu Gly Leu Phe Thr Val Leu
            500                 505                 510

Tyr Thr Val Pro Ala Ala Val Val Ala Cys Leu Phe Tyr Glu Gln
        515                 520                 525

His Asn Arg Pro Arg Trp Glu Ala Thr His Asn Cys Pro Cys Leu Arg
    530                 535                 540

Asp Leu Gln Pro Asp Gln Ala Arg Arg Pro Asp Tyr Ala Val Phe Met
545                 550                 555                 560

Leu Lys Tyr Phe Met Cys Leu Val Val Gly Ile Thr Ser Gly Val Trp
                565                 570                 575

Val Trp Ser Gly Lys Thr Leu Glu Ser Trp Arg Ser Leu Cys Thr Arg
            580                 585                 590

Cys Cys Trp Ala Ser Lys Gly Ala Ala Val Gly Gly Ala Gly Ala
    595                 600                 605

Thr Ala Ala Gly Gly Gly Gly Pro Gly Gly Gly Gly Gly Gly
    610                 615                 620

Pro Gly Gly Gly Gly Pro Gly Gly Gly Gly Ser Leu Tyr Ser
625                 630                 635                 640

Asp Val Ser Thr Gly Leu Thr Trp Arg Ser Gly Thr Ala Ser Ser Val
                645                 650                 655

Ser Tyr Pro Lys Gln Met Pro Leu Ser Gln Val
            660                 665
```

<210> SEQ ID NO 3
<211> LENGTH: 275
<212> TYPE: PRT
<213> ORGANISM: Homo sapiens
<220> FEATURE:
<221> NAME/KEY: misc_feature
<222> LOCATION: (1)..(275)
<223> OTHER INFORMATION: Full-length human Fzd8 ECD (with signal peptide); SP-hFzd8-ECD.275

<400> SEQUENCE: 3

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Gly Glu Gln Pro
                165                 170                 175

Pro Ser Gly Ser Gly His Gly Arg Pro Pro Gly Ala Arg Pro Pro His
            180                 185                 190

Arg Gly Gly Gly Arg Gly Gly Gly Gly Asp Ala Ala Ala Pro Pro
        195                 200                 205

Ala Arg Gly Gly Gly Gly Gly Lys Ala Arg Pro Pro Gly Gly Gly
    210                 215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255

Ile Ala Asn Cys Ala Leu Pro Cys His Asn Pro Phe Phe Ser Gln Asp
            260                 265                 270

Glu Arg Ala
        275

<210> SEQ ID NO 4
<211> LENGTH: 248
<212> TYPE: PRT
<213> ORGANISM: Homo sapiens
<220> FEATURE:
<221> NAME/KEY: misc_feature
<222> LOCATION: (1)..(248)
<223> OTHER INFORMATION: Full-length human Fzd8 ECD (without signal peptide); hFzd8-ECD.275

<400> SEQUENCE: 4

```
Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65              70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr Ala Ala Pro Ser Pro Pro Arg Arg Leu Pro Pro Pro Pro
130                 135                 140

Pro Gly Glu Gln Pro Ser Gly Ser Gly His Gly Arg Pro Pro Gly
145                 150                 155                 160

Ala Arg Pro Pro His Arg Gly Gly Gly Arg Gly Gly Gly Gly Gly Asp
                165                 170                 175

Ala Ala Ala Pro Pro Ala Arg Gly Gly Gly Gly Gly Gly Lys Ala Arg
            180                 185                 190

Pro Pro Gly Gly Gly Ala Ala Pro Cys Glu Pro Gly Cys Gln Cys Arg
            195                 200                 205

Ala Pro Met Val Ser Val Ser Ser Glu Arg His Pro Leu Tyr Asn Arg
        210                 215                 220

Val Lys Thr Gly Gln Ile Ala Asn Cys Ala Leu Pro Cys His Asn Pro
225                 230                 235                 240

Phe Phe Ser Gln Asp Glu Arg Ala
                245

<210> SEQ ID NO 5
<211> LENGTH: 362
<212> TYPE: PRT
<213> ORGANISM: Homo sapiens
<220> FEATURE:
<221> NAME/KEY: misc_feature
<222> LOCATION: (1)..(362)
<223> OTHER INFORMATION: hFzd8-ECD.155-Fc with GS linker

<400> SEQUENCE: 5

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65              70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110
```

```
Glu Gln Gly Asn Pro Asp Thr Leu Cys Met Asp Tyr Asn Arg Thr Asp
            115                 120                 125
Gly Ser Glu Pro Lys Ser Ser Asp Lys Thr His Thr Cys Pro Pro Cys
        130                 135                 140
Pro Ala Pro Glu Leu Leu Gly Gly Pro Ser Val Phe Leu Phe Pro Pro
145                 150                 155                 160
Lys Pro Lys Asp Thr Leu Met Ile Ser Arg Thr Pro Glu Val Thr Cys
                165                 170                 175
Val Val Val Asp Val Ser His Glu Asp Pro Glu Val Lys Phe Asn Trp
            180                 185                 190
Tyr Val Asp Gly Val Glu Val His Asn Ala Lys Thr Lys Pro Arg Glu
        195                 200                 205
Glu Gln Tyr Asn Ser Thr Tyr Arg Val Val Ser Val Leu Thr Val Leu
    210                 215                 220
His Gln Asp Trp Leu Asn Gly Lys Glu Tyr Lys Cys Lys Val Ser Asn
225                 230                 235                 240
Lys Ala Leu Pro Ala Pro Ile Glu Lys Thr Ile Ser Lys Ala Lys Gly
                245                 250                 255
Gln Pro Arg Glu Pro Gln Val Tyr Thr Leu Pro Pro Ser Arg Asp Glu
            260                 265                 270
Leu Thr Lys Asn Gln Val Ser Leu Thr Cys Leu Val Lys Gly Phe Tyr
        275                 280                 285
Pro Ser Asp Ile Ala Val Glu Trp Glu Ser Asn Gly Gln Pro Glu Asn
    290                 295                 300
Asn Tyr Lys Thr Thr Pro Pro Val Leu Asp Ser Asp Gly Ser Phe Phe
305                 310                 315                 320
Leu Tyr Ser Lys Leu Thr Val Asp Lys Ser Arg Trp Gln Gln Gly Asn
                325                 330                 335
Val Phe Ser Cys Ser Val Met His Glu Ala Leu His Asn His Tyr Thr
            340                 345                 350
Gln Lys Ser Leu Ser Leu Ser Pro Gly Lys
        355                 360

<210> SEQ ID NO 6
<211> LENGTH: 389
<212> TYPE: PRT
<213> ORGANISM: Homo sapiens
<220> FEATURE:
<221> NAME/KEY: misc_feature
<222> LOCATION: (1)..(389)
<223> OTHER INFORMATION: SP-hFzd8-ECD.155-Fc with GS linker

<400> SEQUENCE: 6

Met Glu Trp Gly Tyr Leu Leu Glu Val Thr Ser Leu Leu Ala Ala Leu
1               5                   10                  15
Ala Leu Leu Gln Arg Ser Ser Gly Ala Ala Ala Ser Ala Lys Glu
            20                  25                  30
Leu Ala Cys Gln Glu Ile Thr Val Pro Leu Cys Lys Gly Ile Gly Tyr
        35                  40                  45
Asn Tyr Thr Tyr Met Pro Asn Gln Phe Asn His Asp Thr Gln Asp Glu
    50                  55                  60
Ala Gly Leu Glu Val His Gln Phe Trp Pro Leu Val Glu Ile Gln Cys
65                  70                  75                  80
Ser Pro Asp Leu Lys Phe Phe Leu Cys Ser Met Tyr Thr Pro Ile Cys
                85                  90                  95
Leu Glu Asp Tyr Lys Lys Pro Leu Pro Pro Cys Arg Ser Val Cys Glu
```

```
                    100                 105                 110
Arg Ala Lys Ala Gly Cys Ala Pro Leu Met Arg Gln Tyr Gly Phe Ala
            115                 120                 125

Trp Pro Asp Arg Met Arg Cys Asp Arg Leu Pro Glu Gln Gly Asn Pro
130                 135                 140

Asp Thr Leu Cys Met Asp Tyr Asn Arg Thr Asp Gly Ser Glu Pro Lys
145                 150                 155                 160

Ser Ser Asp Lys Thr His Thr Cys Pro Pro Cys Pro Ala Pro Glu Leu
                165                 170                 175

Leu Gly Gly Pro Ser Val Phe Leu Phe Pro Pro Lys Pro Lys Asp Thr
            180                 185                 190

Leu Met Ile Ser Arg Thr Pro Glu Val Thr Cys Val Val Val Asp Val
            195                 200                 205

Ser His Glu Asp Pro Glu Val Lys Phe Asn Trp Tyr Val Asp Gly Val
210                 215                 220

Glu Val His Asn Ala Lys Thr Lys Pro Arg Glu Glu Gln Tyr Asn Ser
225                 230                 235                 240

Thr Tyr Arg Val Val Ser Val Leu Thr Val Leu His Gln Asp Trp Leu
                245                 250                 255

Asn Gly Lys Glu Tyr Lys Cys Lys Val Ser Asn Lys Ala Leu Pro Ala
            260                 265                 270

Pro Ile Glu Lys Thr Ile Ser Lys Ala Lys Gly Gln Pro Arg Glu Pro
            275                 280                 285

Gln Val Tyr Thr Leu Pro Pro Ser Arg Asp Glu Leu Thr Lys Asn Gln
            290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Thr Thr
                325                 330                 335

Pro Pro Val Leu Asp Ser Asp Gly Ser Phe Phe Leu Tyr Ser Lys Leu
            340                 345                 350

Thr Val Asp Lys Ser Arg Trp Gln Gln Gly Asn Val Phe Ser Cys Ser
            355                 360                 365

Val Met His Glu Ala Leu His Asn His Tyr Thr Gln Lys Ser Leu Ser
370                 375                 380

Leu Ser Pro Gly Lys
385

<210> SEQ ID NO 7
<211> LENGTH: 27
<212> TYPE: PRT
<213> ORGANISM: Artificial Sequence
<220> FEATURE:
<223> OTHER INFORMATION: Synthetic peptide: hFzd8 signal peptide

<400> SEQUENCE: 7

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala
            20                  25

<210> SEQ ID NO 8
<211> LENGTH: 232
<212> TYPE: PRT
<213> ORGANISM: Artificial Sequence
<220> FEATURE:
<223> OTHER INFORMATION: Synthetic peptide: Fc C237S
```

-continued

<400> SEQUENCE: 8

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 9
<211> LENGTH: 228
<212> TYPE: PRT
<213> ORGANISM: Artificial Sequence
<220> FEATURE:
<223> OTHER INFORMATION: Synthetic peptide: Exemplary Fc #1

<400> SEQUENCE: 9

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 10
<211> LENGTH: 229
<212> TYPE: PRT
<213> ORGANISM: Artificial Sequence
<220> FEATURE:
<223> OTHER INFORMATION: Synthetic peptide: Exemplary Fc #2

<400> SEQUENCE: 10

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 11
<211> LENGTH: 233

-continued

```
<212> TYPE: PRT
<213> ORGANISM: Artificial Sequence
<220> FEATURE:
<223> OTHER INFORMATION: Synthetic peptide: Fc C237S with N-terminal GS
      linker

<400> SEQUENCE: 11

Gly Ser Glu Pro Lys Ser Ser Asp Lys Thr His Thr Cys Pro Pro Cys
1               5                   10                  15

Pro Ala Pro Glu Leu Leu Gly Gly Pro Ser Val Phe Leu Phe Pro Pro
                20                  25                  30

Lys Pro Lys Asp Thr Leu Met Ile Ser Arg Thr Pro Glu Val Thr Cys
            35                  40                  45

Val Val Val Asp Val Ser His Glu Asp Pro Glu Val Lys Phe Asn Trp
        50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Asp Glu
130                 135                 140

Leu Thr Lys Asn Gln Val Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 12
<211> LENGTH: 128
<212> TYPE: PRT
<213> ORGANISM: Homo sapiens
<220> FEATURE:
<221> NAME/KEY: misc_feature
<222> LOCATION: (1)..(128)
<223> OTHER INFORMATION: hFzd8-ECD.155

<400> SEQUENCE: 12

Ala Ser Ala Lys Glu Leu Ala Cys Gln Glu Ile Thr Pro Leu Cys
1               5                   10                  15

Lys Gly Ile Gly Tyr Asn Tyr Thr Tyr Met Pro Asn Gln Phe Asn His
                20                  25                  30

Asp Thr Gln Asp Glu Ala Gly Leu Glu Val His Gln Phe Trp Pro Leu
            35                  40                  45

Val Glu Ile Gln Cys Ser Pro Asp Leu Lys Phe Phe Leu Cys Ser Met
        50                  55                  60

Tyr Thr Pro Ile Cys Leu Glu Asp Tyr Lys Lys Pro Leu Pro Pro Cys
65                  70                  75                  80
```

-continued

```
Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125
```

<210> SEQ ID NO 13
<211> LENGTH: 155
<212> TYPE: PRT
<213> ORGANISM: Homo sapiens
<220> FEATURE:
<221> NAME/KEY: misc_feature
<222> LOCATION: (1)..(155)
<223> OTHER INFORMATION: SP-hFzd8-ECD.155

<400> SEQUENCE: 13

```
Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp
145                 150                 155
```

<210> SEQ ID NO 14
<211> LENGTH: 508
<212> TYPE: PRT
<213> ORGANISM: Homo sapiens
<220> FEATURE:
<221> NAME/KEY: misc_feature
<222> LOCATION: (1)..(508)
<223> OTHER INFORMATION: hFzd8-ECD.275-Fc

<400> SEQUENCE: 14

```
Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95
```

```
Leu Glu Asp Tyr Lys Lys Pro Leu Pro Pro Cys Arg Ser Val Cys Glu
                100             105                 110

Arg Ala Lys Ala Gly Cys Ala Pro Leu Met Arg Gln Tyr Gly Phe Ala
            115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Gly Glu Gln Pro
                165                 170                 175

Pro Ser Gly Ser Gly His Gly Arg Pro Pro Gly Ala Arg Pro Pro His
            180                 185                 190

Arg Gly Gly Gly Arg Gly Gly Gly Gly Asp Ala Ala Ala Pro Pro
            195                 200                 205

Ala Arg Gly Gly Gly Gly Gly Gly Lys Ala Arg Pro Pro Gly Gly Gly
225 210             215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255

Ile Ala Asn Cys Ala Leu Pro Cys His Asn Pro Phe Phe Ser Gln Asp
            260                 265                 270

Glu Arg Ala Gly Ser Glu Pro Lys Ser Ser Asp Lys Thr His Thr Cys
            275                 280                 285

Pro Pro Cys Pro Ala Pro Glu Leu Leu Gly Gly Pro Ser Val Phe Leu
    290                 295                 300

Phe Pro Pro Lys Pro Lys Asp Thr Leu Met Ile Ser Arg Thr Pro Glu
305                 310                 315                 320

Val Thr Cys Val Val Val Asp Val Ser His Glu Asp Pro Glu Val Lys
                325                 330                 335

Phe Asn Trp Tyr Val Asp Gly Val Glu Val His Asn Ala Lys Thr Lys
            340                 345                 350

Pro Arg Glu Glu Gln Tyr Asn Ser Thr Tyr Arg Val Val Ser Val Leu
            355                 360                 365

Thr Val Leu His Gln Asp Trp Leu Asn Gly Lys Glu Tyr Lys Cys Lys
            370                 375                 380

Val Ser Asn Lys Ala Leu Pro Ala Pro Ile Glu Lys Thr Ile Ser Lys
385                 390                 395                 400

Ala Lys Gly Gln Pro Arg Glu Pro Gln Val Tyr Thr Leu Pro Pro Ser
                405                 410                 415

Arg Asp Glu Leu Thr Lys Asn Gln Val Leu Thr Cys Leu Val Lys Gly
            420                 425                 430

Phe Tyr Pro Ser Asp Ile Ala Val Glu Trp Glu Ser Asn Gly Gln Pro
            435                 440                 445

Glu Asn Asn Tyr Lys Thr Thr Pro Pro Val Leu Asp Ser Asp Gly Ser
    450                 455                 460

Phe Phe Leu Tyr Ser Lys Leu Thr Val Asp Lys Ser Arg Trp Gln Gln
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Pro Gly Lys
            500                 505
```

-continued

```
<210> SEQ ID NO 15
<211> LENGTH: 481
<212> TYPE: PRT
<213> ORGANISM: Homo sapiens
<220> FEATURE:
<221> NAME/KEY: misc_feature
<222> LOCATION: (1)..(481)
<223> OTHER INFORMATION: SP-hFzd8-ECD.275-Fc

<400> SEQUENCE: 15
```

| Ala | Ser | Ala | Lys | Glu | Leu | Ala | Cys | Gln | Glu | Ile | Thr | Val | Pro | Leu | Cys |
|---|---|---|---|---|---|---|---|---|---|---|---|---|---|---|---|
| 1 | | | | 5 | | | | | 10 | | | | | 15 | |

| Lys | Gly | Ile | Gly | Tyr | Asn | Tyr | Thr | Tyr | Met | Pro | Asn | Gln | Phe | Asn | His |
|---|---|---|---|---|---|---|---|---|---|---|---|---|---|---|---|
| | | | 20 | | | | | 25 | | | | | 30 | | |

| Asp | Thr | Gln | Asp | Glu | Ala | Gly | Leu | Glu | Val | His | Gln | Phe | Trp | Pro | Leu |
|---|---|---|---|---|---|---|---|---|---|---|---|---|---|---|---|
| | | | 35 | | | | | 40 | | | | | 45 | | |

| Val | Glu | Ile | Gln | Cys | Ser | Pro | Asp | Leu | Lys | Phe | Phe | Leu | Cys | Ser | Met |
|---|---|---|---|---|---|---|---|---|---|---|---|---|---|---|---|
| | 50 | | | | | 55 | | | | | 60 | | | | |

| Tyr | Thr | Pro | Ile | Cys | Leu | Glu | Asp | Tyr | Lys | Lys | Pro | Leu | Pro | Pro | Cys |
|---|---|---|---|---|---|---|---|---|---|---|---|---|---|---|---|
| 65 | | | | | 70 | | | | | 75 | | | | | 80 |

| Arg | Ser | Val | Cys | Glu | Arg | Ala | Lys | Ala | Gly | Cys | Ala | Pro | Leu | Met | Arg |
|---|---|---|---|---|---|---|---|---|---|---|---|---|---|---|---|
| | | | | 85 | | | | | 90 | | | | | 95 | |

| Gln | Tyr | Gly | Phe | Ala | Trp | Pro | Asp | Arg | Met | Arg | Cys | Asp | Arg | Leu | Pro |
|---|---|---|---|---|---|---|---|---|---|---|---|---|---|---|---|
| | | | 100 | | | | | 105 | | | | | 110 | | |

| Glu | Gln | Gly | Asn | Pro | Asp | Thr | Leu | Cys | Met | Asp | Tyr | Asn | Arg | Thr | Asp |
|---|---|---|---|---|---|---|---|---|---|---|---|---|---|---|---|
| | | | 115 | | | | | 120 | | | | | 125 | | |

| Leu | Thr | Thr | Ala | Ala | Pro | Ser | Pro | Pro | Arg | Arg | Leu | Pro | Pro | Pro | Pro |
|---|---|---|---|---|---|---|---|---|---|---|---|---|---|---|---|
| | 130 | | | | | 135 | | | | | 140 | | | | |

| Pro | Gly | Glu | Gln | Pro | Pro | Ser | Gly | Ser | Gly | His | Gly | Arg | Pro | Pro | Gly |
|---|---|---|---|---|---|---|---|---|---|---|---|---|---|---|---|
| 145 | | | | | 150 | | | | | 155 | | | | | 160 |

| Ala | Arg | Pro | Pro | His | Arg | Gly | Gly | Gly | Arg | Gly | Gly | Gly | Gly | Gly | Asp |
|---|---|---|---|---|---|---|---|---|---|---|---|---|---|---|---|
| | | | | 165 | | | | | 170 | | | | | 175 | |

| Ala | Ala | Ala | Pro | Pro | Ala | Arg | Gly | Gly | Gly | Gly | Gly | Lys | Ala | Arg |
|---|---|---|---|---|---|---|---|---|---|---|---|---|---|---|
| | | | 180 | | | | | 185 | | | | | 190 | |

| Pro | Pro | Gly | Gly | Gly | Ala | Ala | Pro | Cys | Glu | Pro | Gly | Cys | Gln | Cys | Arg |
|---|---|---|---|---|---|---|---|---|---|---|---|---|---|---|---|
| | | | 195 | | | | | 200 | | | | | 205 | | |

| Ala | Pro | Met | Val | Ser | Val | Ser | Ser | Glu | Arg | His | Pro | Leu | Tyr | Asn | Arg |
|---|---|---|---|---|---|---|---|---|---|---|---|---|---|---|---|
| | 210 | | | | | 215 | | | | | 220 | | | | |

| Val | Lys | Thr | Gly | Gln | Ile | Ala | Asn | Cys | Ala | Leu | Pro | Cys | His | Asn | Pro |
|---|---|---|---|---|---|---|---|---|---|---|---|---|---|---|---|
| 225 | | | | | 230 | | | | | 235 | | | | | 240 |

| Phe | Phe | Ser | Gln | Asp | Glu | Arg | Ala | Gly | Ser | Glu | Pro | Lys | Ser | Ser | Asp |
|---|---|---|---|---|---|---|---|---|---|---|---|---|---|---|---|
| | | | | 245 | | | | | 250 | | | | | 255 | |

| Lys | Thr | His | Thr | Cys | Pro | Pro | Cys | Pro | Ala | Pro | Glu | Leu | Leu | Gly | Gly |
|---|---|---|---|---|---|---|---|---|---|---|---|---|---|---|---|
| | | | 260 | | | | | 265 | | | | | 270 | | |

| Pro | Ser | Val | Phe | Leu | Phe | Pro | Pro | Lys | Pro | Lys | Asp | Thr | Leu | Met | Ile |
|---|---|---|---|---|---|---|---|---|---|---|---|---|---|---|---|
| | | 275 | | | | | 280 | | | | | 285 | | | |

| Ser | Arg | Thr | Pro | Glu | Val | Thr | Cys | Val | Val | Val | Asp | Val | Ser | His | Glu |
|---|---|---|---|---|---|---|---|---|---|---|---|---|---|---|---|
| | | 290 | | | | | 295 | | | | | 300 | | | |

| Asp | Pro | Glu | Val | Lys | Phe | Asn | Trp | Tyr | Val | Asp | Gly | Val | Glu | Val | His |
|---|---|---|---|---|---|---|---|---|---|---|---|---|---|---|---|
| 305 | | | | | 310 | | | | | 315 | | | | | 320 |

| Asn | Ala | Lys | Thr | Lys | Pro | Arg | Glu | Glu | Gln | Tyr | Asn | Ser | Thr | Tyr | Arg |
|---|---|---|---|---|---|---|---|---|---|---|---|---|---|---|---|
| | | | | 325 | | | | | 330 | | | | | 335 | |

| Val | Val | Ser | Val | Leu | Thr | Val | Leu | His | Gln | Asp | Trp | Leu | Asn | Gly | Lys |
|---|---|---|---|---|---|---|---|---|---|---|---|---|---|---|---|
| | | | 340 | | | | | 345 | | | | | 350 | | |

| Glu | Tyr | Lys | Cys | Lys | Val | Ser | Asn | Lys | Ala | Leu | Pro | Ala | Pro | Ile | Glu |
|---|---|---|---|---|---|---|---|---|---|---|---|---|---|---|---|
| | | 355 | | | | | 360 | | | | | 365 | | | |

```
Lys Thr Ile Ser Lys Ala Lys Gly Gln Pro Arg Glu Pro Gln Val Tyr
            370                 375                 380

Thr Leu Pro Pro Ser Arg Asp Glu Leu Thr Lys Asn Gln Val Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
                420                 425                 430

Asp Ser Asp Gly Ser Phe Phe Leu Tyr Ser Lys Leu Thr Val Asp Lys
            435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys
```

```
<210> SEQ ID NO 16
<211> LENGTH: 389
<212> TYPE: PRT
<213> ORGANISM: Homo sapiens
<220> FEATURE:
<221> NAME/KEY: misc_feature
<222> LOCATION: (1)..(389)
<223> OTHER INFORMATION: Fzd5 ECD-Fc

<400> SEQUENCE: 16
```

```
Met Ala Arg Pro Asp Pro Ser Ala Pro Pro Ser Leu Leu Leu Leu Leu
1               5                   10                  15

Leu Ala Gln Leu Val Gly Arg Ala Ala Ala Ser Lys Ala Pro Val
            20                  25                  30

Cys Gln Glu Ile Thr Val Pro Met Cys Arg Gly Ile Gly Tyr Asn Leu
            35                  40                  45

Thr His Met Pro Asn Gln Phe Asn His Asp Thr Gln Asp Glu Ala Gly
        50                  55                  60

Leu Glu Val His Gln Phe Trp Pro Leu Val Glu Ile Gln Cys Ser Pro
65                  70                  75                  80

Asp Leu Arg Phe Phe Leu Cys Ser Met Tyr Thr Pro Ile Cys Leu Pro
                85                  90                  95

Asp Tyr His Lys Pro Leu Pro Pro Cys Arg Ser Val Cys Glu Arg Ala
                100                 105                 110

Lys Ala Gly Cys Ser Pro Leu Met Arg Gln Tyr Gly Phe Ala Trp Pro
            115                 120                 125

Glu Arg Met Ser Cys Asp Arg Leu Pro Val Leu Gly Arg Asp Ala Glu
130                 135                 140

Val Leu Cys Met Asp Tyr Asn Arg Ser Glu Gly Pro Ala Glu Pro Lys
145                 150                 155                 160

Ser Ser Asp Lys Thr His Thr Cys Pro Pro Cys Pro Ala Pro Glu Leu
                165                 170                 175

Leu Gly Gly Pro Ser Val Phe Leu Phe Pro Pro Lys Pro Lys Asp Thr
            180                 185                 190

Leu Met Ile Ser Arg Thr Pro Glu Val Thr Cys Val Val Val Asp Val
            195                 200                 205

Ser His Glu Asp Pro Glu Val Lys Phe Asn Trp Tyr Val Asp Gly Val
        210                 215                 220

Glu Val His Asn Ala Lys Thr Lys Pro Arg Glu Glu Gln Tyr Asn Ser
225                 230                 235                 240
```

```
Thr Tyr Arg Val Val Ser Val Leu Thr Val Leu His Gln Asp Trp Leu
                245                 250                 255

Asn Gly Lys Glu Tyr Lys Cys Lys Val Ser Asn Lys Ala Leu Pro Ala
            260                 265                 270

Pro Ile Glu Lys Thr Ile Ser Lys Ala Lys Gly Gln Pro Arg Glu Pro
            275                 280                 285

Gln Val Tyr Thr Leu Pro Pro Ser Arg Asp Glu Leu Thr Lys Asn Gln
        290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Thr Thr
                325                 330                 335

Pro Pro Val Leu Asp Ser Asp Gly Ser Phe Phe Leu Tyr Ser Lys Leu
            340                 345                 350

Thr Val Asp Lys Ser Arg Trp Gln Gln Gly Asn Val Phe Ser Cys Ser
            355                 360                 365

Val Met His Glu Ala Leu His Asn His Tyr Thr Gln Lys Ser Leu Ser
370                 375                 380

Leu Ser Pro Gly Lys
385

<210> SEQ ID NO 17
<211> LENGTH: 360
<212> TYPE: PRT
<213> ORGANISM: Homo sapiens
<220> FEATURE:
<221> NAME/KEY: misc_feature
<222> LOCATION: (1)..(360)
<223> OTHER INFORMATION: hFzd8-ECD.155-Fc without GS linker

<400> SEQUENCE: 17

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205
```

```
Tyr Asn Ser Thr Tyr Arg Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
                260                 265                 270

Lys Asn Gln Val Ser Leu Thr Cys Leu Val Lys Gly Phe Tyr Pro Ser
275                 280                 285

Asp Ile Ala Val Glu Trp Glu Ser Asn Gly Gln Pro Glu Asn Asn Tyr
        290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
                340                 345                 350

Ser Leu Ser Leu Ser Pro Gly Lys
                355                 360

<210> SEQ ID NO 18
<211> LENGTH: 387
<212> TYPE: PRT
<213> ORGANISM: Homo sapiens
<220> FEATURE:
<221> NAME/KEY: misc_feature
<222> LOCATION: (1)..(387)
<223> OTHER INFORMATION: SP-hFzd8-ECD.155-Fc without GS linker

<400> SEQUENCE: 18

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
            35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
130                 135                 140

Asp Thr Leu Cys Met Asp Tyr Asn Arg Thr Asp Glu Pro Lys Ser Ser
145                 150                 155                 160

Asp Lys Thr His Thr Cys Pro Pro Cys Pro Ala Pro Glu Leu Leu Gly
                165                 170                 175

Gly Pro Ser Val Phe Leu Phe Pro Pro Lys Pro Lys Asp Thr Leu Met
            180                 185                 190

Ile Ser Arg Thr Pro Glu Val Thr Cys Val Val Val Asp Val Ser His
```

-continued

```
            195                 200                 205
Glu Asp Pro Glu Val Lys Phe Asn Trp Tyr Val Asp Gly Val Glu Val
        210                 215                 220
His Asn Ala Lys Thr Lys Pro Arg Glu Glu Gln Tyr Asn Ser Thr Tyr
225                 230                 235                 240
Arg Val Val Ser Val Leu Thr Val Leu His Gln Asp Trp Leu Asn Gly
                245                 250                 255
Lys Glu Tyr Lys Cys Lys Val Ser Asn Lys Ala Leu Pro Ala Pro Ile
                260                 265                 270
Glu Lys Thr Ile Ser Lys Ala Lys Gly Gln Pro Arg Glu Pro Gln Val
            275                 280                 285
Tyr Thr Leu Pro Pro Ser Arg Asp Glu Leu Thr Lys Asn Gln Val Ser
        290                 295                 300
Leu Thr Cys Leu Val Lys Gly Phe Tyr Pro Ser Asp Ile Ala Val Glu
305                 310                 315                 320
Trp Glu Ser Asn Gly Gln Pro Glu Asn Asn Tyr Lys Thr Thr Pro Pro
                325                 330                 335
Val Leu Asp Ser Asp Gly Ser Phe Phe Leu Tyr Ser Lys Leu Thr Val
                340                 345                 350
Asp Lys Ser Arg Trp Gln Gln Gly Asn Val Phe Ser Cys Ser Val Met
            355                 360                 365
His Glu Ala Leu His Asn His Tyr Thr Gln Lys Ser Leu Ser Leu Ser
        370                 375                 380
Pro Gly Lys
385
```

FZD8 EXTRACELLULAR DOMAINS AND FZD8 EXTRACELLULAR DOMAIN FUSION MOLECULES AND TREATMENTS USING SAME

This application claims the benefit of U.S. Provisional Application No. 61/359,214, filed Jun. 28, 2010, which is incorporated by reference herein in its entirety for any purpose.

FIELD OF THE INVENTION

This invention relates in general to treatment of human diseases and pathological conditions. In some embodiments, the present invention relates to methods and compositions in treatments for obesity and obesity-related conditions.

BACKGROUND OF THE INVENTION

Obesity is one of the most serious public health problems today. In addition to being one of the leading preventable causes of death worldwide, obesity is associated with many serious medical conditions, including congestive heart failure, ischemic heart disease, deep vein thrombosis, stroke, diabetes, infertility, high blood pressure, high cholesterol, high triglyceride levels, fatty liver disease, breathing difficulties, osteoarthritis, and some forms of cancer.

The first-line treatment for obesity remains dieting and physical exercise, although the success rate for such regimens is low. The most effective treatment is currently bariatric surgery, in which the size of the stomach is reduced by one of several different means. Bariatric surgery is an expensive treatment, however, and the potential complications, including incisional hernia, infections, and pneumonia, can be serious. In addition, the mortality rate with bariatric surgery is about 2 in 1000.

There is a clear need for less costly and invasive alternative treatments for obesity.

SUMMARY OF THE INVENTION

The invention provides methods and compositions for treating obesity and obesity-related conditions based at least in part on identification that administration of a frizzled-8 (Fzd8) extracellular domain (ECD)-Fc fusion molecule results in significant weight loss, and a reduction in fat mass. Fzd8 presents as an important and advantageous therapeutic target, and the invention provides Fzd8 ECDs, Fzd8 ECD fusion molecules, and antibodies that block ligand binding to Fzd8 as therapeutic agents for use in targeting pathological conditions associated with obesity. Accordingly, the invention provides methods and compositions related to Fzd8.

In some embodiments, methods of treating obesity and/or an obesity-related condition are provided. In some embodiments, an obesity-related condition is selected from heart disease, diabetes, breathing difficulties, osteoarthritis, high blood pressure, high cholesterol, high triglycerides, and high free fatty acids. In some embodiments, methods of lowering a blood glucose level are provided. In some embodiments, methods of reducing NPY expression in the hypothalamus are provided.

In some embodiments, the methods comprise administering to a subject a Fzd8 ECD. In some embodiments, the methods comprise administering to a subject a Fzd8 ECD fusion molecule comprising a Fzd8 ECD and at least one fusion partner. In some embodiments, Fzd8 ECDs are provided. In some embodiments, Fzd8 ECD fusion molecules are provided. In some embodiments, pharmaceutical compositions comprising a Fzd8 ECD and/or a Fzd8 ECD fusion molecule are provided. In some embodiments, polynucleotides comprising nucleic acid sequences that encode the polypeptide portion of a Fzd8 ECD or a Fzd8 ECD fusion molecule are provided. In some embodiments, polynucleotides comprising nucleic acid sequences that encode Fzd8 ECD fusion molecules are provided.

In some embodiments, the Fzd8 ECD has a sequence selected from SEQ ID NOs: 3, 4, 12, and 13. In some embodiments, the Fzd8 ECD consists of a sequence selected from SEQ ID NOs: 3, 4, 12, and 13. In some embodiments, the Fzd8 ECD fusion molecule comprises an amino acid sequence selected from SEQ ID NO.: 5, 6, 14, 15, 17, and 18. In some embodiments, the Fzd8 ECD fusion molecule consists of an amino acid sequence selected from SEQ ID NO.: 5, 6, 14, 15, 17, and 18. In some embodiments, at least one fusion partner is selected from an Fc, albumin, and polyethylene glycol. In some embodiments, at least one fusion partner is Fc. In some embodiments, the Fc of the Fzd8 ECD fusion molecule is an $IgG_1$, $IgG_2$, $IgG_3$ or $IgG_4$ Fc region. In some embodiments, the Fc of the Fzd8 fusion molecule is an $IgG_1$ Fc region. In some embodiments, the Fc of the Fzd8 fusion molecule is an $IgG_1$ C237S Fc region. In some embodiments, the Fc of the Fzd8 fusion molecule is an $IgG_4$ Fc region. In some embodiments, at least one fusion partner is an Fc and polyethylene glycol. In some embodiments, at least one fusion partners is polyethylene glycol. In some embodiments, the Fzd8 ECD or Fzd8 ECD fusion molecule comprises a signal peptide. In some embodiments, the fusion molecule comprises a linker between the Fzd8 ECD and one or more fusion partners. In some embodiments, the Fzd8 ECD fusion molecule is glycosylated and/or sialylated. In some embodiments, the polypeptide portion of the fusion molecule is expressed in Chinese hamster ovary (CHO) cells.

In some embodiments, a Fzd8 ECD or Fzd8 ECD fusion molecule lowers blood glucose levels when administered to a subject. In some embodiments, a Fzd8 ECD or Fzd8 ECD fusion molecule reduces NPY expression when administered to a subject. In some embodiments, a Fzd8 ECD or Fzd8 ECD fusion molecule reduces NPY expression when administered to a mouse.

Any embodiment described herein or any combination thereof applies to any and all Fzd8 ECDs or Fzd8 ECD fusion molecules, methods and uses of the invention described herein.

BRIEF DESCRIPTION OF THE DRAWINGS

FIG. 2A shows serum triglyceride levels. FIG. 2B shows cholesterol levels. FIG. 2C shows free fatty acid (FFA) levels.

FIG. 8A shows the weight of food consumed. FIG. 8B shows the percent food consumed by Fzd8-treated mice relative to vehicle-treated mice.

DETAILED DESCRIPTION

Figure 1:
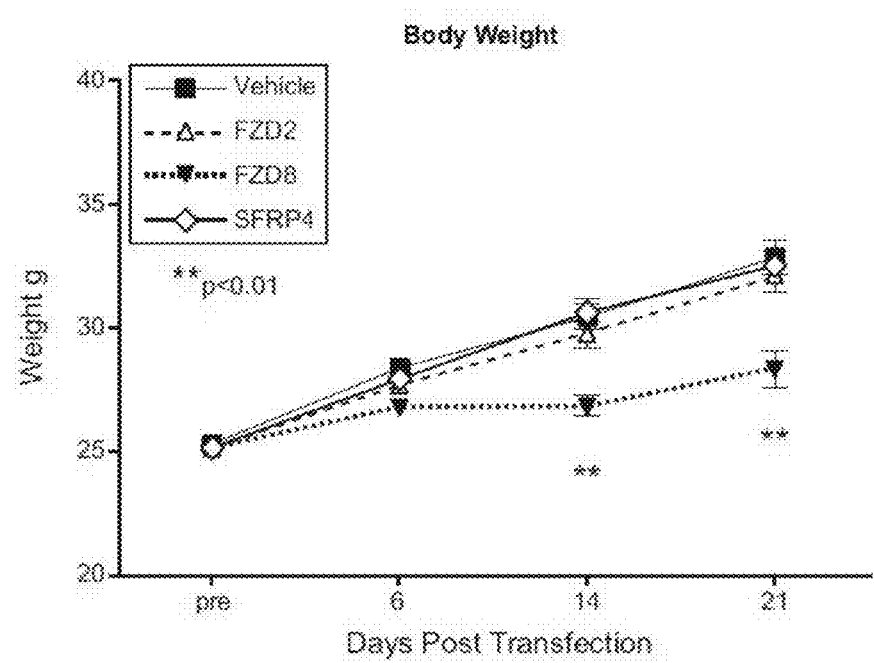
FIG. 1 shows the body weight over time of mice fed a high-fat diet after receiving vehicle, Fzd2 ECD-Fc, Fzd8 ECD-Fc, or SFRP4 ECD-Fc by hydrodynamic tail vein transfection, as described in Example 1.

The section headings used herein are for organizational purposes only and are not to be construed as limiting the subject matter described.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Certain techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning. A Laboratory Manual* (2nd ed., Cold Spring Harbor Laboratory Press, Cold Spring Harbor, N.Y. (1989)), among other places. In addition, certain techniques for chemical syntheses, chemical analyses, pharmaceutical preparation, formulation, and delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "Frizzled-8" or "Fzd8" refer herein to the full-length Fzd8 protein, which includes the N-terminal ECD, the transmembrane domain, and the intracellular domain, with or without an N-terminal signal peptide. In some embodiments, Fzd8 is a human Fzd8. In some embodiments, human Fzd8 has an amino acid sequence corresponding to SEQ ID NO.: 1 or to SEQ ID NO.: 2.

The term "Fzd8 extracellular domain" ("Fzd8 ECD") includes full-length Fzd8 ECDs, Fzd8 ECD fragments, and Fzd8 ECD variants. As used herein, the term "Fzd8 ECD" refers to a Fzd8 polypeptide that lacks the intracellular and transmembrane domains, with or without a signal peptide. In some embodiment, the Fzd8 ECD is a human full-length Fzd8 ECD having an amino acid sequence corresponding to SEQ ID NO.: 3 or to SEQ ID NO: 4. The term "full-length Fzd8 ECD", as used herein, refers to a Fzd8 ECD that extends to the last amino acid of the extracellular domain, and may or may not include an N-terminal signal peptide. As defined herein, the last amino acid of the full-length Fzd8 ECD is at position 275. Thus, a human full-length Fzd8 ECD may consist of the amino acid sequence corresponding to SEQ ID NO.: 4 (mature form) or to SEQ ID NO.: 3 (with the signal peptide). As used herein, the term "Fzd8 ECD fragment" refers to a Fzd8 ECD having one or more residues deleted from the N and/or C terminus of the full-length ECD and that retains the ability to bind to a Wnt ligand. In some embodiments, a Fzd8 fragment retains the ability to bind to at least one ligand selected from Wnt1, Wnt2, Wnt3, Wnt3a, and Wnt7b. The Fzd8 ECD fragment may or may not include an N-terminal signal peptide. In some embodiments, the Fzd8 ECD fragment is a human Fzd8 ECD fragment having an amino acid sequence corresponding to SEQ ID NO.: 12 (mature form) or to SEQ ID NO.: 13 (with the signal peptide). As used herein, the term "Fzd8 ECD variants" refers to Fzd8 ECDs that contain amino acid additions, deletions, and substitutions and that remain capable of binding to a Wnt ligand. Such variants may be at least 90%, 92%, 95%, 97%, 98%, or 99% identical to the parent Fzd8 ECD. The % identity of two polypeptides can be measured by a similarity score determined by comparing the amino acid sequences of the two polypeptides using the Bestfit program with the default settings for determining similarity. Bestfit uses the local homology algorithm of Smith and Waterman, *Advances in Applied Mathematics* 2:482-489 (1981) to find the best segment of similarity between two sequences.

A polypeptide having an amino acid sequence at least, for example, 95% identical to a reference amino acid sequence of a Fzd8 ECD polypeptide is one in which the amino acid sequence of the polypeptide is identical to the reference sequence except that the polypeptide sequence may include up to five amino acid alterations per each 100 amino acids of the reference polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids, up to 5% of the total amino acid residues in the reference sequence, may be inserted into the reference sequence. These alterations of the reference sequence may occur at the N- or C-terminal positions of the reference amino acid sequence or anywhere between those terminal positions, interspersed either individually among residues in the reference sequence, or in one or more contiguous groups within the reference sequence.

As a practical matter, whether any particular polypeptide is at least 70%, 80%, 90%, or 95% identical to, for instance, an amino acid sequence or to a polypeptide sequence encoded by a nucleic acid sequence set forth in the Sequence Listing can be determined conventionally using known computer programs, such the Bestfit program. When using Bestfit or other sequence alignment program to determine whether a particular sequence is, for instance, 95% identical to a reference sequence according to the present invention, the parameters are set, of course, that the percentage of identity is calculated over the full length of the reference amino acid sequence and that gaps in homology of up to 5% of the total number of amino acid residues in the reference sequence are allowed.

As used herein, the terms "hFzd8-ECD.275" and "hFzd8.275" may be used interchangeably to refer to the full-length human Fzd8 ECD corresponding to SEQ ID NO: 3 (with signal peptide) or to SEQ ID NO: 4 (without signal peptide; mature form).

As used herein, the terms "hFzd8-ECD.155" and "hFzd8.155" may be used interchangeably to refer to the human Fzd8 ECD corresponding to SEQ ID NO: 13 (with signal peptide) or to SEQ ID NO: 12 (without signal peptide; mature form).

The term "Fzd8 ECD fusion molecule" refers to a molecule comprising a Fzd8 ECD, and one or more "fusion partners." In some embodiment, the Fzd8 ECD and the fusion partner are covalently linked ("fused"). If the fusion partner is also a polypeptide ("the fusion partner polypeptide"), the Fzd8 ECD and the fusion partner polypeptide may be part of a continuous amino acid sequence, and the fusion partner polypeptide may be linked to either the N terminus or the C terminus of the Fzd8 ECD. In such cases, the Fzd8 ECD and the fusion partner polypeptide may be translated as a single polypeptide from a coding sequence that encodes both the Fzd8 ECD and the fusion partner polypeptide (the "Fzd8 ECD fusion protein"). In some embodiments, the Fzd8 ECD and the fusion partner are covalently linked through other means, such as, for example, a chemical linkage other than a peptide bond. Many known methods of covalently linking polypeptides to other molecules (for example, fusion partners) may be used. In other embodiments, the Fzd8 ECD and the fusion partner may be fused through a "linker," which is comprised of at least one amino acid or chemical moiety.

In some embodiments, the Fzd8 polypeptide and the fusion partner are noncovalently linked. In some such embodiments, they may be linked, for example, using binding pairs. Exemplary binding pairs include, but are not limited to, biotin and avidin or streptavidin, an antibody and its antigen, etc.

Exemplary fusion partners include, but are not limited to, an immunoglobulin Fc domain, albumin, and polyethylene glycol. The amino acid sequences of some exemplary Fc domains are shown in SEQ ID NOs: 8 to 10. In some embodiments, there is a two amino acid residue linker consisting of an N-terminal glycine residue followed by a serine residue (GS) located between the Fzd8 ECD and the Fc. The amino acid sequence of a some exemplary N-terminal GS linker followed by an Fc is shown in SEQ ID NO: 11.

The term "signal peptide" refers to a sequence of amino acid residues located at the N terminus of a polypeptide that facilitates secretion of a polypeptide from a mammalian cell. A signal peptide may be cleaved upon export of the polypeptide from the mammalian cell, forming a mature protein. Signal peptides may be natural or synthetic, and they may be heterologous or homologous to the protein to which they are attached. Exemplary signal peptides include, but are not limited to, the signal peptides of Fzd8, such as, for example, the amino acid sequence of SEQ ID NOs: 7. Exemplary signal peptides also include signal peptides from heterologous proteins. A "signal sequence" refers to a polynucleotide sequence that encodes a signal peptide. In some embodiments, a Fzd8 ECD lacks a signal peptide. In some embodiments, a Fzd8 ECD includes at least one signal peptide, which may be a native Fzd8 signal peptide or a heterologous signal peptide.

In some embodiments, a Fzd8 ECD amino acid sequence is derived from that of a non-human mammal. In such embodiments, the Fzd8 ECD amino acid sequence may be derived from mammals including, but not limited to, rodents (including mice, rats, hamsters), rabbits, simians, felines, canines, equines, bovines, porcines, ovines, caprines, mammalian laboratory animals, mammalian farm animals, mammalian sport animals, and mammalian pets. Fzd8 ECD fusion molecules incorporating a non-human Fzd8 ECD are termed "non-human Fzd8 ECD fusion molecules." Similar to the human Fzd8 ECD fusion molecules, non-human fusion molecules may comprise a fusion partner, optional linker, and a Fzd8 ECD. Such non-human fusion molecules may also include a signal peptide. A "non-human Fzd8 ECD fragment" refers to a non-human Fzd8 ECD having one or more residues deleted from the N and/or C terminus of the full-length ECD and that retains the ability to bind to a Wnt ligand of the non-human animal from which the sequence was derived. A "non-human Fzd8 ECD variant" refers to Fzd8 ECDs that contain amino acid additions, deletions, and substitutions and that remain capable of binding to a Wnt ligand from the animal from which the sequence was derived.

The term "antibody" as used herein refers to a molecule comprising at least complementarity-determining region (CDR)1, CDR2, and CDR3 of a heavy chain and at least CDR1, CDR2, and CDR3 of a light chain, wherein the molecule is capable of binding to antigen. The term antibody includes, but is not limited to, fragments that are capable of binding antigen, such as Fv, single-chain Fv (scFv), Fab, Fab', and (Fab')$_2$. The term antibody also includes, but is not limited to, chimeric antibodies, humanized antibodies, and antibodies of various species such as mouse, human, cynomolgus monkey, etc.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells; plant cells; and insect cells. Exemplary mammalian cells include, but are not limited to, 293 and CHO cells, and their derivatives, such as 293-6E and DG44 cells, respectively.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The terms "subject" and "patient" are used interchangeably herein to refer to a human. In some embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided.

The term "obesity" refers to a medical condition that includes an accumulation of excess body fat such that an obese individual has a body mass index (BMI) of greater than 25. In some embodiments, an obese individual has a BMI of greater than 26, greater than 27, greater than 28, greater than 29, or greater than 30. BMI may be calculated using standard methods, such as BMI=((weight in pounds)$_{x703}$)/(height in inches)$^2$.

The term "obesity-related condition" refers to a condition that is associated with obesity. Such conditions include, but are not limited to, heart disease, diabetes (such as type 2 diabetes), breathing difficulties, osteoarthritis, high blood pressure, high cholesterol (including high LDL cholesterol), high triglycerides, and high free fatty acids.

"Treatment" (and grammatical variations thereof such as "treat" or "treating"), as used herein, includes any administration or application of a therapeutic for condition in a mammal, including a human, and includes inhibiting the condition or progression of the condition, inhibiting or slowing the condition or its progression, arresting its development, partially or fully relieving the condition, or curing the condition, for example, by causing regression, or restoring or repairing a lost, missing, or defective function; or stimulating an inefficient process.

In the case of obesity, a treatment includes any administration or application of a therapeutic that results in at least a 10% reduction in body weight. In some embodiments, a treatment results in at least a 10% increase in the ratio of lean mass to fat mass in a subject.

The terms "inhibition" or "inhibit" refer to a decrease or cessation of any phenotypic characteristic or to the decrease or cessation in the incidence, degree, or likelihood of that characteristic.

An agent is said to "lower blood glucose levels" or "lower a blood glucose level," if the agent lowers blood glucose levels in a subject by at least 15% after administration of the agent, relative to blood glucose levels in the subject before administration of the agent. In some embodiments, an agent lowers blood glucose levels by at least 20%, at least 25%, at least 30%, or at least 35% after administration. In some embodiments, "after administration" is 8 hours, 12 hours, 24 hours, 2 days, 3 days, 5 days, 1 week, 10 days, 2 weeks, or 1 month after first administration of the agent.

An agent is said to "lower fasting blood glucose levels" or "lower a fasting blood glucose level," if the agent lowers fasting blood glucose levels in a subject by at least 15% after administration of the agent, relative to fasting blood glucose levels in the subject before administration of the agent. In some embodiments, an agent lowers fasting blood glucose levels by at least 20%, at least 25%, at least 30%, or at least 35% after administration. In some embodiments, "after administration" is 8 hours, 12 hours, 24 hours, 2 days, 3 days, 5 days, 1 week, 10 days, 2 weeks, or 1 month after first administration of the agent. In some embodiments, the length of the fast prior to measuring fasting blood glucose levels is at least 4 hours, at least 6 hours, at least 8 hours, at least 12 hours, at least 18 hours, or at least 24 hours.

An agent is said to "reduce NPY expression" if the agent reduces the levels of NPY mRNA and/or protein in the hypothalamus of a test animal after administration of the agent, relative to the levels of NPY mRNA and/or protein in the hypothalamus of an untreated test animal. In some embodiments, an agent reduces the levels of NPY mRNA and/or protein by at least 15%, at least 20%, at least 25%, at least 30%, or at least 35% after administration. In some embodiments, "after administration" is 8 hours, 12 hours, 24 hours, 2 days, 3 days, 5 days, 1 week, 10 days, 2 weeks, or 1 month after first administration of the agent. Nonlimiting exemplary test animals include rodents (such as mice and rats), simians, felines, canines, equines, bovines, porcines, ovines, and caprines.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

Therapeutic Compositions and Methods

Methods of Treating Conditions using Fzd8 ECDs and Fzd8 ECD Fusion Molecules

Methods of treating obesity and obesity-related conditions comprising administering a Fzd8 ECD, Fzd8 ECD fusion molecule, and/or an antibody that binds Fzd8 are provided. Nonlimiting exemplary Fzd8 ECDs that are useful for treating obesity and obesity-related conditions include ECDs having a sequence selected from SEQ ID NOs: 3, 4, 12, and 16. Nonlimiting exemplary Fzd8 ECD fusion molecules that are useful for treating obesity and obesity-related conditions include fusion molecules having a sequence selected from SEQ ID NOs: 5, 6, 14, 15, 17, and 18.

Exemplary obesity-related conditions that may be treated with a Fzd8 ECD, Fzd8 ECD fusion molecule, and/or an antibody that binds Fzd8 include, but are not limited to, heart disease, diabetes (such as type 2 diabetes), breathing difficulties, osteoarthritis, high blood pressure, high cholesterol (including high LDL cholesterol), high triglycerides, and high free fatty acids.

Methods of lowering blood glucose levels in a subject comprising administering a Fzd8 ECD, Fzd8 ECD fusion molecule, and/or an antibody that binds Fzd8 are also provided. In some embodiments, methods of lowering fasting blood glucose levels in a subject comprising administering a Fzd8 ECD, Fzd8 ECD fusion molecule, and/or an antibody that binds Fzd8 are provided. Nonlimiting exemplary Fzd8 ECDs that are useful for lowering blood glucose levels include ECDs having a sequence selected from SEQ ID NOs: 3, 4, 12, and 16. Nonlimiting exemplary Fzd8 ECD fusion molecules that are useful for treating obesity and obesity-related conditions include fusion molecules having a sequence selected from SEQ ID NOs: 5, 6, 14, 15, 17, and 18.

Methods of reducing NPY expression in the hypothalamus of a subject comprising administering a Fzd8 ECD, Fzd8 ECD fusion molecule, and/or an antibody that binds Fzd8 are also provided. Nonlimiting exemplary Fzd8 ECDs that are useful for lowering blood glucose levels include ECDs having a sequence selected from SEQ ID NOs: 3, 4, 12, and 16. Nonlimiting exemplary Fzd8 ECD fusion molecules that are useful for treating obesity and obesity-related conditions include fusion molecules having a sequence selected from SEQ ID NOs: 5, 6, 14, 15, 17, and 18.

Routes of Administration and Carriers

In some embodiments, a Fzd8 ECD, a Fzd8 ECD fusion molecule, and/or an antibody that binds Fzd8 is administered subcutaneously. In some embodiments, a Fzd8 ECD, a Fzd8 ECD fusion molecule, and/or an antibody that binds Fzd8 is administered intravenously. In some embodiments, a Fzd8 ECD, a Fzd8 ECD fusion molecule, and/or an antibody that binds Fzd8 may be administered in vivo by various routes, including, but not limited to, oral, intra-arterial, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. One or more nucleic acid molecules that encode a Fzd8 ECD, a Fzd8 ECD fusion molecule, and/or an antibody that binds Fzd8 may be coated onto gold microparticles and delivered intradermally by a particle bombardment device, or "gene gun," as described in the literature (see, e.g., Tang et al., *Nature* 356:152-154 (1992)). The appropriate formulation and route of administration may be selected according to the intended application.

In various embodiments, compositions comprising Fzd8 ECDs, Fzd8 ECD fusion molecules, and/or an antibodies that bind Fzd8 are provided in formulations with a wide variety of pharmaceutically acceptable carriers (see, e.g., Gennaro, *Remington: The Science and Practice of Pharmacy with Facts and Comparisons: Drugfacts Plus,* 20th ed. (2003); Ansel et al., *Pharmaceutical Dosage Forms and Drug Delivery Systems,* $7^{th}$ ed., Lippencott Williams and Wilkins (2004); Kibbe et al., *Handbook of Pharmaceutical Excipients,* $3^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Nonlimiting exemplary carriers include saline, buffered saline, dextrose, water, glycerol, ethanol, and combinations thereof.

In various embodiments, compositions comprising Fzd8 ECDs, Fzd8 ECD fusion molecules, and/or an antibodies that bind Fzd8 may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Nonlimiting exemplary methods of making such formulations are described, for example, in EP 1 125 584 A1.

Pharmaceutical packs and kits comprising one or more containers, each containing one or more doses of a Fzd8 ECD, a Fzd8 ECD fusion molecule, and/or an antibody to Fzd8 are also provided. In some embodiments, a unit dosage is provided wherein the unit dosage contains a predetermined amount of a composition comprising a Fzd8 ECD, a Fzd8 ECD fusion molecule, and/or an antibody to Fzd8, with or without one or more additional agents. In some embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in some embodiments, the composition may be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition of the invention comprises heparin and/or a proteoglycan.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In general, the Fzd8 ECDs, Fzd8 ECD fusion molecules, and antibodies to Fzd8 may be administered in an amount in the range of about 10 µg/kg body weight to about 100 mg/kg body weight per dose. In some embodiments, the Fzd8 ECDs, Fzd8 ECD fusion molecules, and antibodies to Fzd8 may be administered in an amount in the range of about 50 µg/kg body weight to about 5 mg/kg body weight per dose. In some embodiments, the Fzd8 ECDs, Fzd8 ECD fusion molecules, and antibodies to Fzd8 may be administered in an amount in the range of about 100 µg/kg body weight to about 10 mg/kg body weight per dose. In some embodiments, the Fzd8 ECDs, Fzd8 ECD fusion molecules, and antibodies to Fzd8 may be administered in an amount in the range of about 100 µg/kg body weight to about 20 mg/kg body weight per dose. In some embodiments, the Fzd8 ECDs, Fzd8 ECD fusion molecules, and antibodies to Fzd8 may be administered in an amount in the range of about 0.5 mg/kg body weight to about 20 mg/kg body weight per dose.

The Fzd8 ECD, Fzd8 ECD fusion molecule, or antibody to Fzd8 compositions may be administered as needed to subjects. Determination of the frequency of administration may be made by persons skilled in the art, such as an attending physician based on considerations of the condition being treated, age of the subject being treated, severity of the condition being treated, general state of health of the subject being treated and the like. In some embodiments, an effective dose of the Fzd8 ECD, Fzd8 ECD fusion molecule, and/or antibody to Fzd8 is administered to a subject one or more times. In various embodiments, an effective dose of the Fzd8 ECD, Fzd8 ECD fusion molecule, and/or antibody to Fzd8 is administered to the subject once a month, more than once a month, such as, for example, every two months or every three months. In some embodiments, an effective dose of the Fzd8 ECD, Fzd8 ECD fusion molecule, and/or antibody to Fzd8 is administered less than once a month, such as, for example, every three weeks, every two weeks or every week. An effective dose of the Fzd8 ECD, Fzd8 ECD fusion molecule, and/or antibody to Fzd8 is administered to the subject at least once. In some embodiments, the effective dose of the Fzd8 ECD, Fzd8 ECD fusion molecule, and/or antibody to Fzd8 may be administered multiple times, including for periods of at least a month, at least six months, or at least a year.

Combination Therapy

Fzd8 ECDs, Fzd8 ECD fusion molecules, and/or antibodies to Fzd8 may be administered alone or with other modes of treatment. They may be provided before, substantially contemporaneous with, or after other modes of treatment, for example, diet, physical exercise, surgery, or the administration of another therapeutic molecule. In some embodiments, a Fzd8 ECD, Fzd8 ECD fusion molecule, and/or antibody to Fzd8 is administered with an appetite suppressant. Nonlimiting exemplary therapeutic molecules that may be administered with a Fzd8 ECD, Fzd8 ECD fusion molecule, and/or antibody to Fzd8 include phentermine, Xenical® (orlistat), Meridia® (sibutramin HCl monohydrate), Alli® (orlistat), lorcaserin, Qnexa® (phentermine/topiramate), Contrave® (naltrexone SR/bupropion SR), Victoza (liraglutide), cetilistat, Symlin with metreleptin (pramlintide/metreleptin), Histalean (betahistine), Empatic™ (zonisamide SR/bupropion SR), tesofensine, SLx-4090 (Surface Logix), AR9281 (Arete), velneperit, davalintide, TTP435 (TransTech), TM30339 (7™ Pharma), and obinepitide.

Fzd8 Extracellular Domains

Nonlimiting exemplary Fzd8 ECDs include full-length Fzd8 ECDs, Fzd8 ECD fragments, and Fzd8 ECD variants. Fzd8 ECDs may include or lack a signal peptide. Exemplary Fzd8 ECDs include, but are not limited to, Fzd8 ECDs having amino acid sequences selected from SEQ ID NOs: 3, 4, 12, and 13. In some embodiments, a Fzd8 ECD is isolated. In some embodiments, an Fzd8 ECD binds at least one ligand selected from Wnt1, Wnt2, Wnt3, Wnt3a, and Wnt7b.

In some embodiments, administration of a human Fzd8 ECD fusion molecule to mice fed a normal diet results in weight loss and reduced fat pad weights. In addition, administration of a human Fzd8 ECD fusion molecule to mice fed a high fat diet results in very little weight gain (compared to a gain of about 30% body weight in vehicle-treated mice), reduced fat mass, and increased lean to fat ratio. Further, mice administered a Fzd8 ECD fusion molecule consumed less than vehicle-treated mice, but had normal digestive tracks.

Fzd8 ECD Fragments

Non-limiting exemplary Fzd8 ECD fragments include human Fzd8 ECD ending at amino acid 155 (counting from the first amino acid of the signal peptide, whether or not the signal peptide is present). In some embodiments, a Fzd8 ECD fragment ends at an amino acid between amino acid 155 and amino acid 275.

Fzd8 ECD fragments may include or lack a signal peptide. Exemplary Fzd8 ECD fragments include, but are not limited to, Fzd8 ECD fragments having amino acid sequences selected from SEQ ID NOs: 12 and 13. In some embodiments, an Fzd8 ECD fragment binds at least one ligand selected from Wnt1, Wnt2, Wnt3, Wnt3a, and Wnt7b.

Fusion Partners and Conjugates

As discussed, a Fzd8 ECD of the present invention may be combined with a fusion partner polypeptide, resulting in a Fzd8 ECD fusion protein. These fusion partner polypeptides may facilitate purification, and the Fzd8 ECD fusion proteins may show an increased half-life in vivo. Fusion partner polypeptides that have a disulfide-linked dimeric structure due to the IgG portion may also be more efficient in binding and neutralizing other molecules than the monomeric Fzd8 ECD fusion protein or the Fzd8 ECD alone. Suitable fusion partners of a Fzd8 ECD include, for example, polymers, such as water soluble polymers, the constant domain of immunoglobulins; all or part of human serum albumin (HSA); fetuin A; fetuin B; a leucine zipper domain; a tetranectin trimerization domain; mannose binding protein (also known as mannose binding lectin), for example, mannose binding protein 1; and an Fc region, as described herein and further described in U.S. Pat. No. 6,686,179.

A Fzd8 ECD fusion molecule of the invention may be prepared by attaching polyaminoacids or branch point amino acids to the Fzd8 ECD. For example, the polyaminoacid may be a carrier protein that serves to increase the circulation half life of the Fzd8 ECD (in addition to the advantages achieved via a fusion molecule). For the therapeutic purpose of the present invention, such polyaminoacids should ideally be those that have or do not create neutralizing antigenic response, or other adverse responses. Such polyaminoacids may be chosen from serum album (such as HSA), an additional antibody or portion thereof, for example the Fc region, fetuin A, fetuin B, leucine zipper nuclear factor erythroid derivative-2 (NFE2), neuroretinal leucine zipper, tetranectin, or other polyaminoacids, for example, lysines. As described herein, the location of attachment of the polyaminoacid may be at the N terminus or C terminus, or other places in between, and also may be connected by a chemical linker moiety to the selected molecule.

Polymers

Polymers, for example, water soluble polymers, are useful in the present invention as the Fzd8 ECD to which the polymer is attached will not precipitate in an aqueous environment, such as typically found in a physiological environment. Polymers employed in the invention will be pharmaceutically acceptable for the preparation of a therapeutic product or composition.

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1,3-dioxolane, poly-1,3,6-trioxane, ethylene/maleic anhydride copolymer, poly(β-amino acids) (either homopolymers or random copolymers), poly(n-vinyl pyrrolidone) polyethylene glycol, polypropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll, or dextran and mixtures thereof.

As used herein, polyethylene glycol (PEG) is meant to encompass any of the forms that have been used to derivatize other proteins, such as mono-(C1-C10) alkoxy- or aryloxy-polyethylene glycol. Polyethylene glycol propionaldehyde may have advantages in manufacturing due to its stability in water.

Polymers used herein, for example water soluble polymers, may be of any molecular weight and may be branched or unbranched. In some embodiments, the polymers have an average molecular weight of between about 2 kDa to about 100 kDa (the term "about" indicating that in preparations of a polymer, some molecules will weigh more, some less, than the stated molecular weight). The average molecular weight of each polymer may be between about 5 kDa and about 50 kDa, or between about 12 kDa and about 25 kDa. Generally, the higher the molecular weight or the more branches, the higher the polymer:protein ratio. Other sizes may also be used, depending on the desired therapeutic profile; for example, the duration of sustained release; the effects, if any, on biological activity; the ease in handling; the degree or lack of antigenicity; and other known effects of a polymer on a Fzd8 ECD of the invention.

Polymers employed in the present invention are typically attached to a Fzd8 ECD with consideration of effects on functional or antigenic domains of the polypeptide. In general, chemical derivatization may be performed under any suitable condition used to react a protein with an activated polymer molecule. Activating groups which can be used to link the polymer to the active moieties include sulfone, maleimide, sulfhydryl, thiol, triflate, tresylate, azidirine, oxirane, and 5-pyridyl.

Polymers of the invention are typically attached to a heterologous polypeptide at the alpha (α) or epsilon (ε) amino groups of amino acids or a reactive thiol group, but it is also contemplated that a polymer group could be attached to any reactive group of the protein that is sufficiently reactive to become attached to a polymer group under suitable reaction conditions. Thus, a polymer may be covalently bound to a Fzd8 ECD via a reactive group, such as a free amino or carboxyl group. The amino acid residues having a free amino group may include lysine residues and the N-terminal amino acid residue. Those having a free carboxyl group may include aspartic acid residues, glutamic acid residues, and the C-terminal amino acid residue. Those having a reactive thiol group include cysteine residues.

Methods for preparing fusion molecules conjugated with polymers, such as water soluble polymers, will each generally involve (a) reacting a Fzd8 ECD with a polymer under conditions whereby the polypeptide becomes attached to one or more polymers and (b) obtaining the reaction product. Reaction conditions for each conjugation may be selected from any of those known in the art or those subsequently developed, but should be selected to avoid or limit exposure to reaction conditions such as temperatures, solvents, and pH levels that would inactivate the protein to be modified. In general, the optimal reaction conditions for the reactions will be determined case-by-case based on known parameters and the desired result. For example, the larger the ratio of polymer:polypeptide conjugate, the greater the percentage of conjugated product. The optimum ratio (in terms of efficiency of reaction in that there is no excess unreacted polypeptide or polymer) may be determined by factors such as the desired degree of derivatization (e.g., mono-, di-, tri-, etc.), the molecular weight of the polymer selected, whether the polymer is branched or unbranched and the reaction conditions used. The ratio of polymer (for example, PEG) to a polypeptide will generally range from 1:1 to 100:1. One or more purified conjugates may be prepared from each mixture by standard purification techniques, including among others, dialysis, salting-out, ultrafiltration, ion-exchange chromatography, gel filtration chromatography, and electrophoresis.

One may specifically desire an N-terminal chemically modified Fzd8 ECD. One may select a polymer by molecular weight, branching, etc., the proportion of polymers to Fzd8 ECD molecules in the reaction mix, the type of reaction to be performed, and the method of obtaining the selected N-terminal chemically modified Fzd8 ECD. The method of obtaining the N-terminal chemically modified Fzd8 ECD preparation (separating this moiety from other monoderivatized moieties if necessary) may be by purification of the N-terminal chemically modified Fzd8 ECD material from a population of chemically modified protein molecules.

Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N terminus with a carbonyl group-containing polymer is achieved. For example, one may selectively attach a polymer to the N terminus of the protein by performing the reaction at a pH that allows one to take advantage of the pKa differences between the ε-amino group of the lysine residues and that of the α-amino group of the N-terminal residue of the protein. By such selective derivatization, attachment of a polymer to a protein is controlled: the conjugation with the polymer takes place predominantly at the N terminus of the protein and no significant modification of other reactive groups, such as the lysine side chain amino groups, occurs. Using reductive alkylation, the polymer may be of the type described above and should have a single reactive aldehyde for coupling to the protein. Polyethylene glycol propionaldehyde, containing a single reactive aldehyde, may also be used.

In one embodiment, the present invention contemplates the chemically derivatized Fzd8 ECD to include mono- or poly- (e.g., 2-4) PEG moieties. Pegylation may be carried out by any of the pegylation reactions available. Methods for preparing a pegylated protein product will generally include (a) reacting a polypeptide with polyethylene glycol (such as a reactive ester or aldehyde derivative of PEG) under conditions whereby the protein becomes attached to one or more PEG groups; and (b) obtaining the reaction product(s). In general, the optimal reaction conditions will be determined case by case based on known parameters and the desired result.

There are a number of PEG attachment methods available to those skilled in the art. See, for example, EP 0 401 384; Malik et al., *Exp. Hematol.*, 20:1028-1035 (1992); Francis, *Focus on Growth Factors*, 3(2):4-10 (1992); EP 0 154 316; EP 0 401 384; WO 92/16221; WO 95/34326; and the other publications cited herein that relate to pegylation.

Pegylation may be carried out, e.g., via an acylation reaction or an alkylation reaction with a reactive polyethylene glycol molecule. Thus, protein products according to the present invention include pegylated proteins wherein the PEG group(s) is (are) attached via acyl or alkyl groups. Such products may be mono-pegylated or poly-pegylated (for example, those containing 2-6 or 2-5 PEG groups). The PEG groups are generally attached to the protein at the α- or ε-amino groups of amino acids, but it is also contemplated that the PEG groups could be attached to any amino group attached to the protein that is sufficiently reactive to become attached to a PEG group under suitable reaction conditions.

Pegylation by acylation generally involves reacting an active ester derivative of polyethylene glycol (PEG) with a Fzd8 ECD of the invention. For acylation reactions, the polymer(s) selected typically have a single reactive ester group. Any known or subsequently discovered reactive PEG molecule may be used to carry out the pegylation reaction. An example of a suitable activated PEG ester is PEG esterified to N-hydroxysuccinimide (NHS). As used herein, acylation is contemplated to include, without limitation, the following types of linkages between the therapeutic protein and a polymer such as PEG: amide, carbamate, urethane, and the like, see for example, Chamow, *Bioconjugate Chem.*, 5:133-140 (1994). Reaction conditions may be selected from any of those currently known or those subsequently developed, but should avoid conditions such as temperature, solvent, and pH that would inactivate the polypeptide to be modified.

Pegylation by acylation will generally result in a poly-pegylated protein. The connecting linkage may be an amide. The resulting product may be substantially only (e.g., >95%) mono-, di-, or tri-pegylated. However, some species with higher degrees of pegylation may be formed in amounts depending on the specific reaction conditions used. If desired, more purified pegylated species may be separated from the mixture (particularly unreacted species) by standard purification techniques, including among others, dialysis, salting-out, ultrafiltration, ion-exchange chromatography, gel filtration chromatography, and electrophoresis.

Pegylation by alkylation generally involves reacting a terminal aldehyde derivative of PEG with a polypeptide in the presence of a reducing agent. For the reductive alkylation reaction, the polymer(s) selected should have a single reactive aldehyde group. An exemplary reactive PEG aldehyde is polyethylene glycol propionaldehyde, which is water stable, or mono C1-C10 alkoxy or aryloxy derivatives thereof, see for example, U.S. Pat. No. 5,252,714.

Markers

Moreover, Fzd8 ECDs of the present invention may be fused to marker sequences, such as a peptide that facilitates purification of the fused polypeptide. The marker amino acid sequence may be a hexa-histidine peptide such as the tag provided in a pQE vector (Qiagen), among others, many of which are commercially available. As described in Gentz et al., *Proc. Natl. Acad. Sci.* 86:821-824 (1989), for instance, hexa-histidine provides for convenient purification of the fusion protein. Another peptide tag useful for purification, the hemagglutinin (HA) tag, corresponds to an epitope derived from the influenza HA protein. (Wilson et al., *Cell* 37:767 (1984)). Any of these above fusions may be engineered using the Fzd8 ECDs of the present invention.

Oligomerization Domain Fusion Partners

In various embodiments, oligomerization offers some functional advantages to a fusion protein, including, but not limited to, multivalency, increased binding strength, and the combined function of different domains. Accordingly, in some embodiments, a fusion partner comprises an oligomerization domain, for example, a dimerization domain. Exemplary oligomerization domains include, but are not limited to, coiled-coil domains, including alpha-helical coiled-coil domains; collagen domains; collagen-like domains; and certain immunoglobulin domains. Exemplary coiled-coil polypeptide fusion partners include, but are not limited to, the tetranectin coiled-coil domain; the coiled-coil domain of cartilage oligomeric matrix protein; angiopoietin coiled-coil domains; and leucine zipper domains. Exemplary collagen or collagen-like oligomerization domains include, but are not limited to, those found in collagens, mannose binding lectin, lung surfactant proteins A and D, adiponectin, ficolin, conglutinin, macrophage scavenger receptor, and emilin.

Antibody Fc Immunoglobulin Domain Fusion Partners

Many Fc domains that may be used as fusion partners are known in the art. In some embodiments, a fusion partner is an Fc immunoglobulin domain. An Fc fusion partner may be a wild-type Fc found in a naturally occurring antibody, a variant thereof, or a fragment thereof. Non-limiting exemplary Fc fusion partners include Fcs comprising a hinge and the CH2 and CH3 constant domains of a human IgG, for example, human IgG1, IgG2, IgG3, or IgG4. Additional exemplary Fc fusion partners include, but are not limited to, human IgA and IgM. In some embodiments, an Fc fusion partner comprises a C237S mutation, for example, in an IgG1. In some embodiments, an Fc fusion partner comprises a hinge, CH2, and CH3 domains of human IgG2 with a P331S mutation, as described in U.S. Pat. No. 6,900,292. Certain exemplary Fc domain fusion partners are shown in SEQ ID NOs: 8 to 11.

Albumin Fusion Partners and Albumin-binding Molecule Fusion Partners

In some embodiments, a fusion partner is an albumin. Exemplary albumins include, but are not limited to, human serum album (HSA) and fragments of HSA that are capable of increasing the serum half-life or bioavailability of the polypeptide to which they are fused. In some embodiments, a fusion partner is an albumin-binding molecule, such as, for example, a peptide that binds albumin or a molecule that conjugates with a lipid or other molecule that binds albumin In some embodiments, a fusion molecule comprising HSA is prepared as described, e.g., in U.S. Pat. No. 6,686,179.

Exemplary Attachment of Fusion Partners

The fusion partner may be attached, either covalently or non-covalently, to the N terminus or the C terminus of the Fzd8 ECD. The attachment may also occur at a location within the Fzd8 ECD other than the N terminus or the C terminus, for example, through an amino acid side chain (such as, for example, the side chain of cysteine, lysine, serine, or threonine).

In either covalent or non-covalent attachment embodiments, a linker may be included between the fusion partner and the Fzd8 ECD. Such linkers may be comprised of at least one amino acid or chemical moiety. Exemplary methods of covalently attaching a fusion partner to a Fzd8 ECD include, but are not limited to, translation of the fusion partner and the Fzd8 ECD as a single amino acid sequence and chemical attachment of the fusion partner to the Fzd8 ECD. When the fusion partner and a Fzd8 ECD are translated as single amino acid sequence, additional amino acids may be included between the fusion partner and the Fzd8 ECD as a linker. In some embodiments, the linker is glycine-serine ("GS"; see, e.g., SEQ ID NO: 11). In some embodiments, the linker is selected based on the polynucleotide sequence that encodes it, to facilitate cloning the fusion partner and/or Fzd8 ECD into a single expression construct (for example, a polynucleotide containing a particular restriction site may be placed between the polynucleotide encoding the fusion partner and the polynucleotide encoding the Fzd8 ECD, wherein the polynucleotide containing the restriction site encodes a short amino acid linker sequence). When the fusion partner and the Fzd8 ECD are covalently coupled by chemical means, linkers of various sizes may typically be included during the coupling reaction.

Exemplary methods of non-covalently attaching a fusion partner to a Fzd8 ECD include, but are not limited to, attachment through a binding pair. Exemplary binding pairs include, but are not limited to, biotin and avidin or streptavidin, an antibody and its antigen, etc.

Antibodies that Block Ligand Binding to Fzd8

In some embodiments, antibodies that block binding of at least one ligand to Fzd8 are provided. In some embodiments, an antibody blocks binding of a ligand selected from Wnt1, Wnt2, Wnt3, Wnt3a, and Wnt7b to Fzd8. See, e.g., PCT Publication No. WO 2007/053577. In some embodiments, an antibody binds to Fzd8 extracellular domain (ECD). In some embodiments, an antibody binds a polypeptide comprising an amino acid sequence selected from SEQ ID NOs: 3, 4, 12, and 13. In some embodiments, an antibody binds a polypeptide consisting of an amino acid sequence selected from SEQ ID NOs: 3, 4, 12, and 13. Nonlimiting exemplary antibodies that bind Fzd8 are described, e.g., in PCT Publication Nos. WO 2007/053577 and WO 2010/037041.

Signal Peptide

In order for some secreted proteins to express and secrete in large quantities, a signal peptide from a heterologous protein may be desirable. Employing heterologous signal peptides may be advantageous in that a resulting mature polypeptide may remain unaltered as the signal peptide is removed in the ER during the secretion process. The addition of a heterologous signal peptide may be required to express and secrete some proteins.

Nonlimiting exemplary signal peptide sequences are described, e.g., in the online Signal Peptide Database maintained by the Department of Biochemistry, National University of Singapore. See Choo et al., *BMC Bioinformatics*, 6: 249 (2005); and PCT Publication No. WO 2006/081430.

Co-Translational and Post-Translational Modifications

The invention encompasses Fzd8 ECDs and Fzd8 ECD fusion molecules that are differentially modified during or after translation, for example by glycosylation, acetylation, phosphorylation, amidation, derivatization by known protecting/blocking groups, proteolytic cleavage, or linkage to an antibody molecule or other cellular ligand. Similarly, antibodies that bind Fzd8 ECD and block binding of at least one ligand to Fzd8 ECD that are differentially modified during or after translation are also provided. Any of numerous chemical modifications may be carried out by known techniques, including, but not limited to, specific chemical cleavage by cyanogen bromide, trypsin, chymotrypsin, papain, V8 protease; $NABH_4$ acetylation; formylation; oxidation; reduction; and/or metabolic synthesis in the presence of tunicamycin.

Additional post-translational modifications encompassed by the invention include, for example, for example, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression Nucleic Acid Molecules Encoding Fzd8 ECDs, Fzd8 ECD Fusion Molecules, and/or Antibodies that Bind Fzd8

Nucleic acid molecules comprising polynucleotides that encode Fzd8 ECDs, Fzd8 ECD fusion molecules, or antibodies that bind Fzd8 ECD are provided. Nucleic acid molecules comprising polynucleotides that encode Fzd8 ECD fusion molecules in which the Fzd8 ECD and the fusion partner are translated as a single polypeptide are also provided. Such nucleic acid molecules may be constructed using recombinant DNA techniques conventional in the art.

In some embodiments, a polynucleotide encoding a Fzd8 ECD comprises a nucleotide sequence that encodes a signal peptide, which, when translated, will be fused to the N terminus of the Fzd8 ECD. As discussed above, the signal peptide may be the native Fzd8 signal peptide, or may be another heterologous signal peptide. In some embodiments, the nucleic acid molecule comprising the polynucleotide encoding the gene of interest is an expression vector that is suitable for expression in a selected host cell.

Fzd8 ECD, Fzd8 ECD Fusion Molecule, and Fzd8 Antibody Expression and Production

Vectors

Vectors comprising polynucleotides that encode Fzd8 ECDs are provided. Vectors comprising polynucleotides that encode Fzd8 ECD fusion molecules are also provided. Vectors comprising polynucleotides that encode one or both chains of an antibody that binds Fzd8 are also provided. Such vectors include, but are not limited to, DNA vectors, phage vectors, viral vectors, retroviral vectors, etc.

In some embodiments, a vector is selected that is optimized for expression of polypeptides in CHO or CHO-derived cells. Exemplary such vectors are described, e.g., in Running Deer et al., *Biotechnol. Prog.* 20:880-889 (2004).

In some embodiments, a vector is chosen for in vivo expression of Fzd8 ECDs and/or Fzd8 ECD fusion molecules and/or antibodies that bind Fzd8 in animals, including humans. In some such embodiments, expression of the polypeptide is under the control of a promoter that functions in a tissue-specific manner. For example, liver-specific promoters are described, e.g., in PCT Publication No. WO 2006/076288.

Host Cells

In various embodiments, Fzd8 ECDs, Fzd8 ECD fusion molecules, or antibodies that bind Fzd8 may be expressed in prokaryotic cells, such as bacterial cells; or in eukaryotic cells, such as fungal cells, plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO—S and DG44 cells; and NS0 cells. In some embodiments, a particular eukaryotic host cell is selected based on its ability to make certain desired post-translational modifications to the Fzd8 ECDs, Fzd8 ECD fusion molecules, or antibodies that bind Fzd8. For example, in some embodiments, CHO cells produce Fzd8 ECDs and/or Fzd8

ECD fusion molecules and/or antibodies that bind Fzd8 that have a higher level of sialylation than the same polypeptide produced in 293 cells.

Introduction of a nucleic acid into a desired host cell may be accomplished by any method known in the art, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., *Molecular Cloning, A Laboratory Manual*, 3$^{rd}$ ed. Cold Spring Harbor Laboratory Press (2001). Nucleic acids may be transiently or stably transfected in the desired host cells, according to methods known in the art.

In some embodiments, a polypeptide may be produced in vivo in an animal that has been engineered or transfected with a nucleic acid molecule encoding the polypeptide, according to methods known in the art.

Purification of Fzd8 ECD Polypeptides

Fzd8 ECDs, Fzd8 ECD fusion molecules, and antibodies that bind Fzd8 may be purified by various methods known in the art. Such methods include, but are not limited to, the use of affinity matrices or hydrophobic interaction chromatography. Suitable affinity ligands include any ligands of the Fzd8 ECD or of the fusion partner, or antibodies thereto. Suitable affinity ligands in the case of an antibody that binds Fzd8 include, but are not limited to, Fzd8 itself and fragments thereof. Further, a Protein A, Protein G, Protein A/G, or an antibody affinity column may be used to bind to an Fc fusion partner to purify a Fzd8 ECD fusion molecule or to the Fc portion of an antibody to Fzd8. Antibodies to Fzd8 ECD may also be used to purify Fzd8 ECD or Fzd8 ECD fusion molecules. Hydrophobic interactive chromatography, for example, a butyl or phenyl column, may also suitable for purifying some polypeptides. Many methods of purifying polypeptides are known in the art.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Mice Treated with Fzd8 ECD-Fc Exhibited Less Weight Gain on a High-Fat Diet than Vehicle-Treated Mice Study Procedure Seven- to eight-week old male C57BL/6 mice (Jackson Labs, Bar Harbor, Me.) were administered a DNA vector encoding Fzd8 ECD-Fc, Fzd2 ECD-Fc, secreted frizzled-related protein 4 (SFRP4) ECD-Fc, or vehicle (Ringer's Solution; Fisher Scientific, Pittsburgh, Pa.; AD-5038) by hydrodynamic tail vein transfection (TVT) substantially as described in Chen et al., *Human Gene Therapy* 16(1): 126-131 (2005). Eleven mice were included in each group, and each mouse (except vehicle-treated mice) received 20 µg of DNA in 2 ml Ringer's Solution by hydrodynamic tail vein transfection. Vehicle-treated mice received 2 ml Ringer's Solution by hydrodynamic tail vein transfection.

Following hydrodynamic tail vein transfection, the mice were switched to a 60% high fat diet (Research Diets Inc., New Brunswick, N.J.; Diet #D12492, 60% kcal fat). Fresh food weight was recorded for each mouse, and the mice were weighed and their food consumption recorded by measuring the difference between what was provided and what was left, every seven days. Mice were monitored for bloody stool and diarrhea on days when food was recorded.

Mice were bled on day 5 to determine plasma protein expression and transfection efficiency. On day 21, body weight and food consumption were recorded. Blood was collected by cardiac puncture at the time of euthanasia with isoflurane for serum chemistry and lipid panels.

Necroscopy was performed following euthanasia to record the weights of the testicular, inguinal, and renal fat pads, and to dissect the colon, caecum, and duodenum for histological analysis. The gastrointestinal tracts were fixed in 4% neutral buffered formalin for 24 hours. Fixed tissues were washed in PBS and stored in 70% ethanol. For histological analysis, the fixed tissues were embedded in paraffin and stained with H&E (hematoxylin and eosin).

Results

FIG. 1 shows body weight of the mice in the study. The mice that received Fzd8 ECD-Fc by TVT had significantly lower body weight by 14 days post-injection than the mice that received Fzd2 ECD-Fc, SFRP ECD-Fc, and vehicle. While the vehicle-, Fzd2 ECD-Fc-, and SFRP ECD-Fc-treated mice all gained about 7 grams (or about 30% of their initial body weight) over the course of the study, the Fzd8-treated mice gained only about 2 grams (approximately 12% of their initial body weight).

Food consumption was monitored at various intervals during the course of the study (data not shown). Fzd8 ECD-Fc-treated mice consumed about 9% less food than vehicle-treated mice on day 5 post injection, about 13% less food on day 14 post injection, and about 11% less food on day 21 post injection. This suggests that Fzd8 treatment may lead to increased satiety signals, lower food consumption, and ultimately a decrease in body weight gain, relative to vehicle treated mice.

Figure 2:
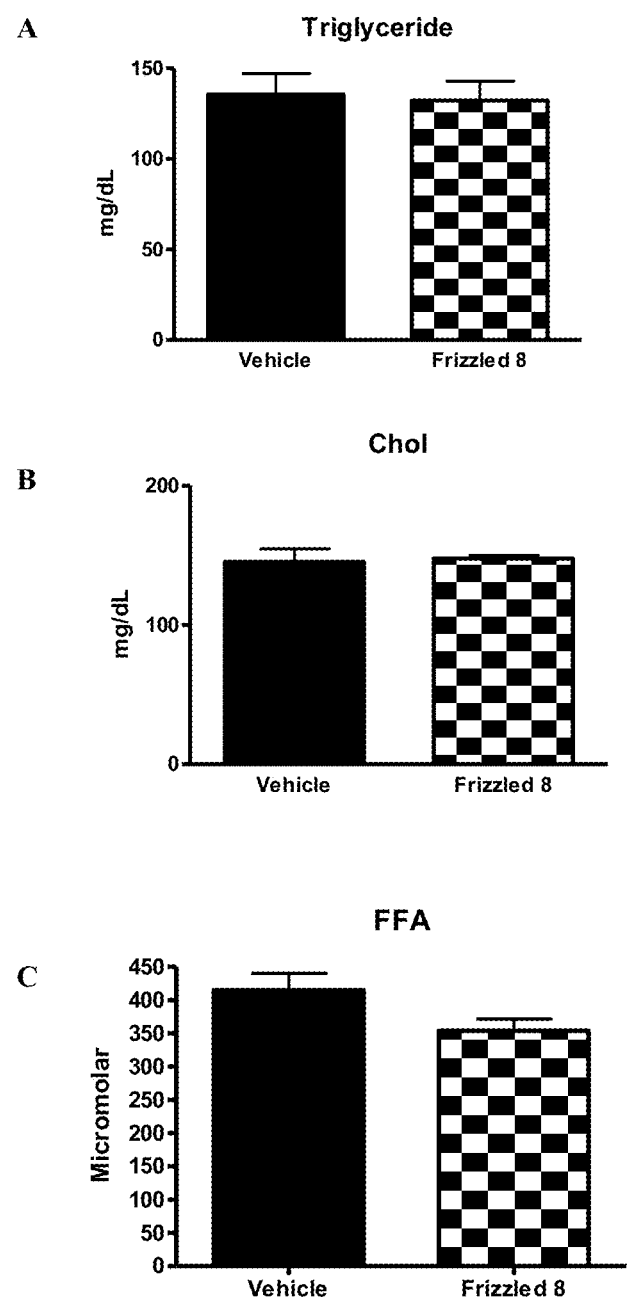
FIG. 2 shows lipid levels in mice fed a high-fat diet after receiving vehicle or Fzd8 ECD-Fc by hydrodynamic tail vein transfection, as described in Example 1.

FIG. 2 shows the results of the lipid panel for the vehicle- and Fzd8 ECD-Fc-treated mice. The Fzd8 ECD-Fc-treated mice showed no reduction in serum triglycerides or cholesterol (FIGS. 2A and 2B), but showed some reduction in serum free fatty acids, with a statistical p value of 0.07 (FIG. 2C).

Figure 3:
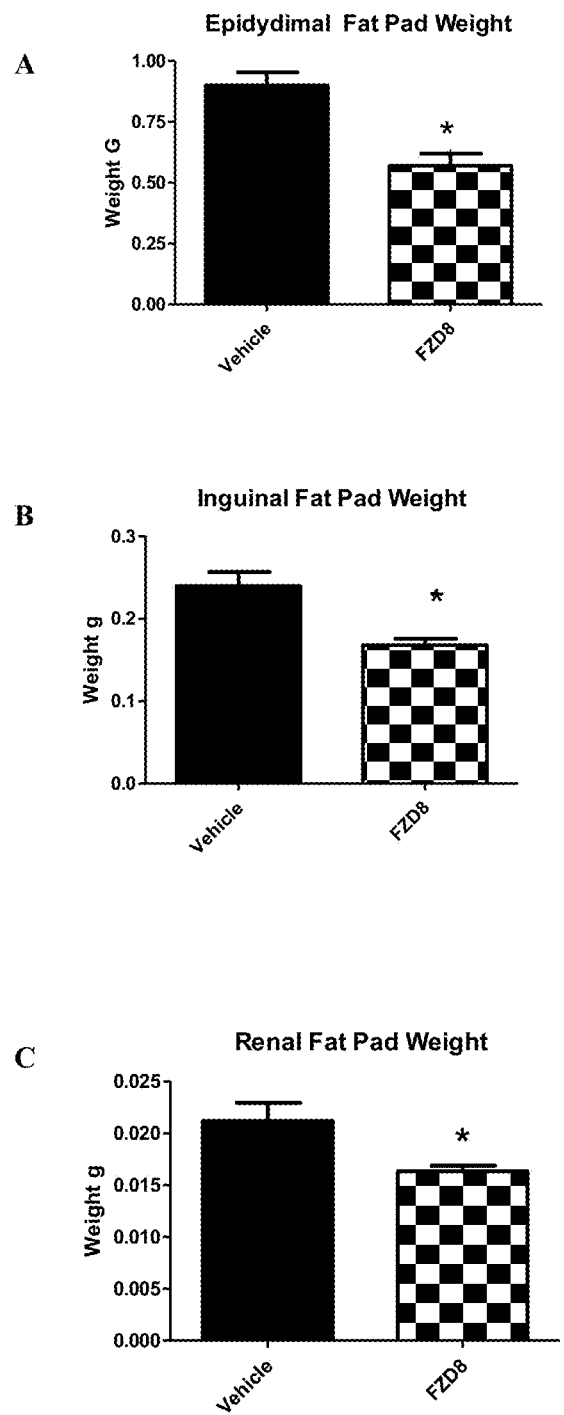
FIG. 3 shows epididymal (A), inguinal (B), and renal (C) fat pad weights in mice fed a high-fat diet after receiving vehicle or Fzd8 ECD-Fc by hydrodynamic tail vein transfection, as described in Example 1.

FIG. 3 shows that the epididymal, inguinal, and renal fat pads of the Fzd8 ECD-Fc-treated mice weighed significantly less (p<0.05) than the fat pads of the vehicle-treated mice.

Figure 4:
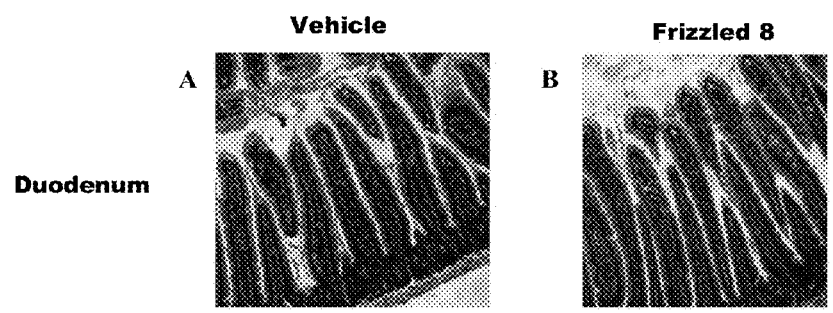
FIG. 4 shows a duodenum from a mouse that received vehicle (A) and a mouse that received Fzd8 ECD-Fc (B) by hydrodynamic tail vein transfection, as described in Example 1.

Finally, the Fzd8 ECD-Fc-treated mice did not display any histological abnormalities in the gastrointestinal tract. FIG. 4 shows the duodenum from a vehicle-treated mouse (A) and a Fzd8 ECD-Fc-treated mouse (B).

Example 2

Mice Treated with Fzd8 ECD-Fc and Fed a High-fat Diet had Higher Lean to Fat Ratio than Vehicle-treated Mice Study Procedure Seven- to eight-week old male C57BL/6 mice (Jackson Labs) were administered Fzd8 ECD-Fc, leucine-rich repeat protein 1 (LRRP1) ECD-Fc, or vehicle (Ringer's Solution; Fisher Scientific; AD-5038) by hydrodynamic tail vein transfection. Twelve mice were included in each group, and each mouse (except vehicle-treated mice) received 20 μg of DNA in 2 ml Ringer's Solution by hydrodynamic tail vein transfection. Vehicle-treated mice received 2 ml Ringer's Solution by hydrodynamic tail vein transfection.

Following hydrodynamic tail vein transfection, the mice were switched to a 60% high fat diet (Purina 60 kCal % Fat Blue Dye, Lot 090406024i). Body weight was recorded weekly. Mice were also monitored for bloody stool and diarrhea on days when weight was recorded. On day 28, the mice were euthanized using isoflurane and cardiac puncture, and blood was collected for serum chemistry and plasma fatty acid analysis.

Necroscopy was performed following euthanasia to collect the duodenum from each mouse for histological analysis. The duodenums were fixed in 4% neutral buffered formalin for 24 hours, washed in PBS, then stored in 70% ethanol. Fixed tissues were embedded in paraffin, cross-sectioned, and stained with H&E (hematoxylin and eosin). As before, no differences were observed between the duodenums of the vehicle-treated and Fzd8 ECD-Fc-treated mice (data not shown).

After tissue collection, the small incision was glued and the vehicle- and Fzd8-treated mice were placed in sealed bags and frozen for MRI analysis of body composition, including fat mass, lean mass, and lean to fat ratio. MRI analysis was done at Echo Medical Systems in Houston, Tex., using an EchoMRI-100.

Results

Figure 5:
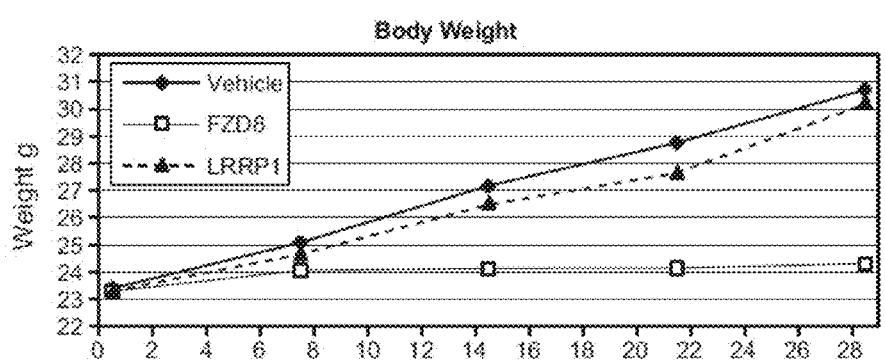
FIG. 5 shows the body weight over time of mice fed a high-fat diet after receiving vehicle, Fzd8 ECD-Fc, or LRRP1 ECD-Fc by hydrodynamic tail vein transfection, as described in Example 2.

FIG. 5 shows body weight of the vehicle-, Fzd8 ECD-Fc-, and leucine-rich repeat protein 1 (LRRP1) ECD-Fc-treated mice over the course of the study. The vehicle- and LRRP1 ECD-Fc-treated mice gained approximately 7 grams, or about 30% of their body weight, during the study. Fzd8 ECD-Fc-treated mice, in contrast, gained only about 1 gram during the study.

Figure 6:
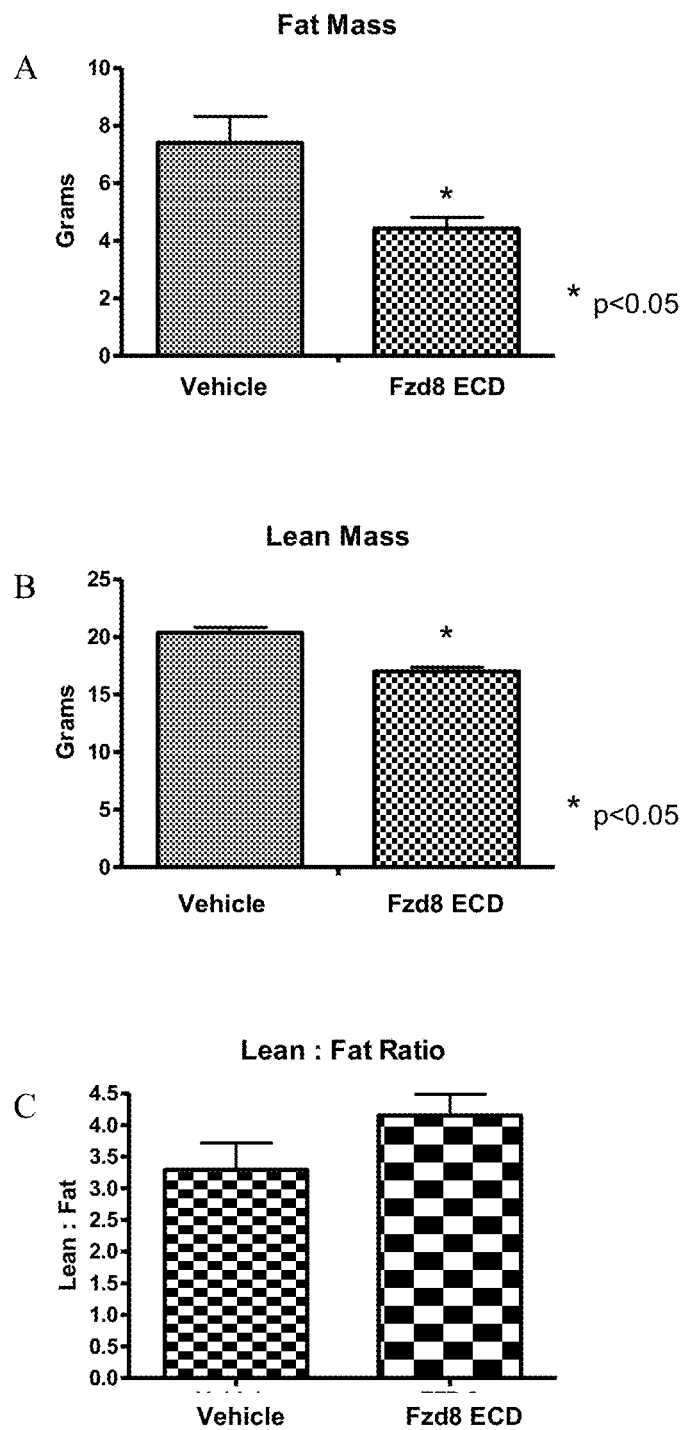
FIG. 6 shows the fat mass (A), lean mass (B), and lean mass to fat mass ratio (C) of mice fed a high-fat diet after receiving vehicle or Fzd8 ECD-Fc by hydrodynamic tail vein transfection, as described in Example 2.

FIG. 6 shows the fat mass, lean mass, and lean to fat ratio of the vehicle- and Fzd8-treated mice. The Fzd8 ECD-Fc-treated mice had significantly decreased fat mass compared to the vehicle-treated mice. See FIG. 6A. The Fzd8 ECD-Fc-treated mice also had an increased lean to fat ratio compared to vehicle-treated mice. See FIG. 6C. Finally, the Fzd8 ECD-Fc-treated mice also had decreased lean mass compared to vehicle-treated mice. See FIG. 6B. The decreased lean mass may be due to a reduced need for lean mass to support overall body mass in the lighter-weight Fzd8 ECD-Fc-treated mice. It should be noted that the study did not show a reduction in overall lean or fat mass, e.g., relative to mice fed a regular diet, but rather an attenuation of growth of lean and fat tissue in Fzd8 ECD-Fc-treated mice fed a high-fat diet relative to vehicle-treated mice also fed a high-fat diet.

Example 3

Mice Treated with Fzd8 ECD-Fc that were Fed a Regular Diet Lost Weight

Study Procedure

Twenty six-week-old male C57BL/6 mice (Charles River Labs) were individually housed for 14 days. On day 15, food consumption measurements were started and conducted twice per week. One week later, ten mice were administered Fzd8 ECD-Fc and ten mice were administered vehicle (0.9% NaCl) by hydrodynamic tail vein transfection. Each Fzd8 ECD-Fc-treated mouse received 20 μg of DNA in 2 ml 0.9% NaCl by hydrodynamic tail vein transfection. Vehicle-treated mice received 2 ml 0.9% NaCl by hydrodynamic tail vein transfection.

Following hydrodynamic tail vein transfection, body weight and food consumption were recorded daily to every other day throughout the study. Mice were bled 5 days post transfection to assay plasma protein expression by ELISA.

On day 20 post transfection, body weight and food consumption were recorded before euthanasia using isoflurane and cardiac puncture. At necropsy, the epididymal fat pad was collected and weighed. Blood was collected in serum separator tubes, allowed to clot at room temperature, and spun for 10 minutes at 10,000 rpm (13,000 xg). Serum was separated and sent to Quality Clinical Labs for serum chemistry analysis of alanine aminotransferase (ALT), aspartate aminotransferase (ALT), potassium (K), calcium (Ca), total protein (PROT-T), albumin (ALB), and globulin (GLOB).

Results

Table 1 shows the level of expression of Fzd8 ECD-Fc in each mouse at 5 days post transfection. Expression levels for animals 1 through 10, which received vehicle, were 0 for each animal, and are not shown in Table 1. Mouse 19 died the day after hydrodynamic tail vein transfection, likely as a result of the procedure. All of the mice expressed Fzd8 ECD-Fc. The upper threshold of the assay was 2500. The expression levels of Fzd8 ECD-Fc in the mice were generally very high.

TABLE 1

| Fzd8 ECD-Fc expression in transfected mice | |
| --- | --- |
| Animal | Expression level |
| 11 | 2500 |
| 12 | 2500 |
| 13 | 2500 |
| 14 | 2500 |
| 15 | 2500 |
| 16 | 790 |
| 18 | 690 |
| 19 | died |
| 20 | 1770 |

Blood was collected at the end of the study for a serum chemistry panel. Table 2 shows the results of that panel. There was no significant difference between vehicle- and Fzd8 ECD-Fc-treated mice for any of the factors tested in the panel.

TABLE 2

| | AST (U/L) | ALT (U/L) | K (mEq/L) | CA (mg/dL) | PROT-T (g/dL) | ALB (g/dL) | GLOB (g/dL) |
| --- | --- | --- | --- | --- | --- | --- | --- |
| | Serum chemistry | | | | | | |
| Vehicle | 89 | 36.2 | 7.04 | 10.16 | 5.26 | 3.54 | 1.72 |
| FZD8 | 88.57143 | 45.85714 | 6.914286 | 10.17143 | 5.128571 | 3.385714 | 1.742857 |
| p Value | 0.979593 | 0.120749 | 0.779125 | 0.946053 | 0.262711 | 0.063217 | 0.775257 |

In addition, the hematocrit for each mouse was determined, and no difference was found between the vehicle-treated mice and the Fzd8 ECD-Fc-treated mice (data not shown). Finally, no gross changes in the mice were observed, nor any differences between the vehicle- and Fzd8 ECD-Fc-treated mice.

Figure 7:
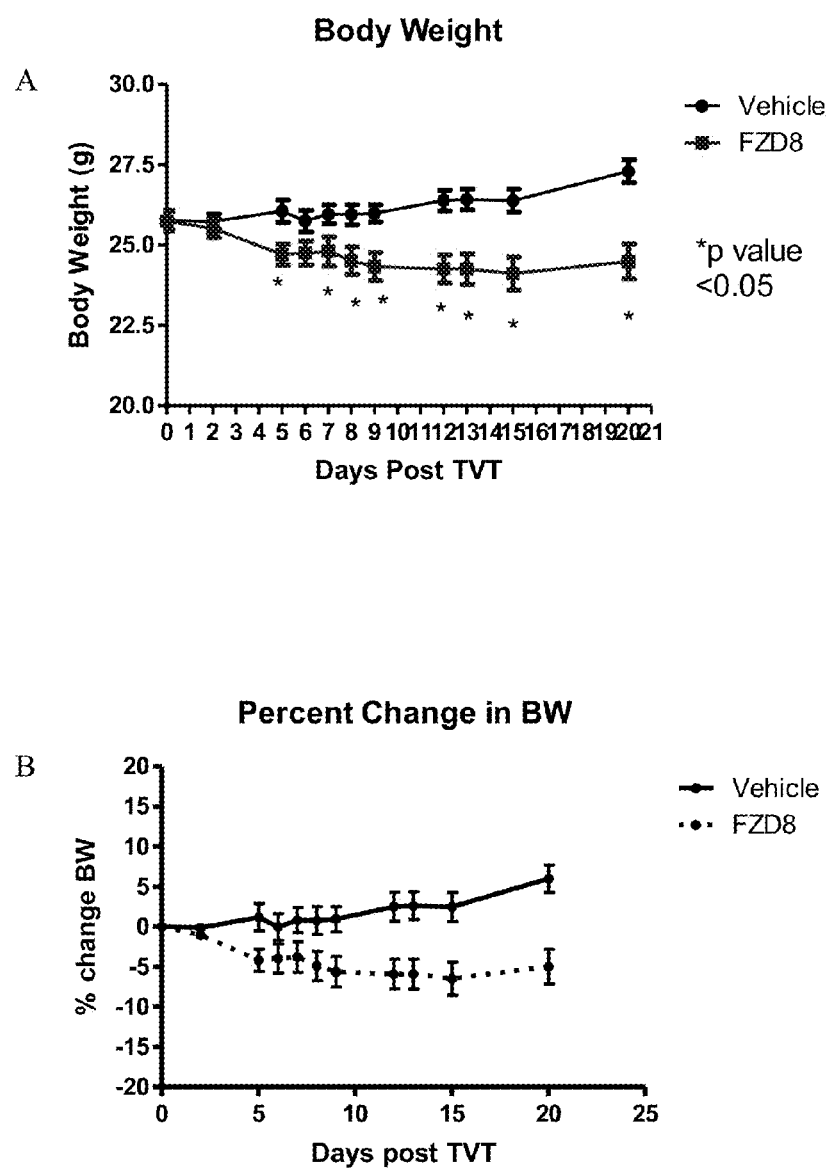
FIG. 7 shows the body weight (A) and percent change in body weight (B) over time of mice fed a regular diet after receiving vehicle or Fzd8 ECD-Fc by hydrodynamic tail vein transfection (TVT), as described in Example 3.

FIG. 7 shows body weight of the vehicle- and Fzd8 ECD-Fc-treated mice over the course of the study. The vehicle-treated mice gained 1 to 2 grams over the course of the study, while the Fzd8 ECD-Fc-treated mice lost 1 to 2 grams. See FIG. 7A. This corresponds to a gain of about 5% of their body weight for the vehicle-treated mice, and a loss of about 5% of their body weight for the Fzd8 ECD-Fc-treated mice. See FIG. 7B.

Figure 8:
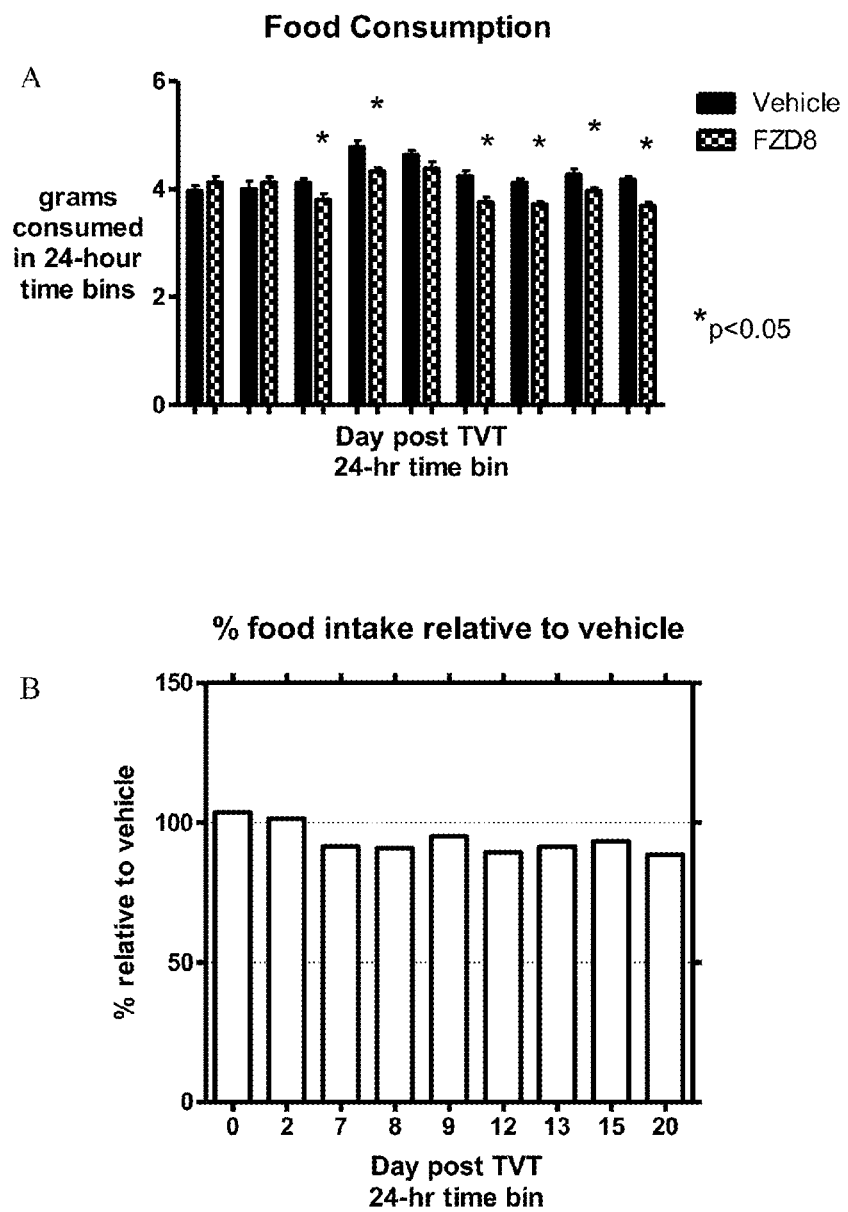
FIG. 8 shows the food consumption over time of mice fed a regular diet after receiving vehicle or Fzd8 ECD-Fc by hydrodynamic tail vein transfection, as described in Example 3.

FIG. 8 shows food consumption of the vehicle- and Fzd8 ECD-Fc-treated mice over the course of the study. After day 7, the Fzd8 ECD-Fc-treated animals ate significantly less than the vehicle-treated mice for most of the periods tested during the remainder of the study. See FIG. 8A. The Fzd8 ECD-Fc-treated mice had about 90% of the food intake of the vehicle-treated mice from day 7 through the end of the study. See FIG. 8B. These results suggest that Fzd8 ECD-Fc treatment may lead to increased satiety signals, less food consumption, and ultimately a decrease in body weight gain, relative to vehicle treated mice.

Figure 9:
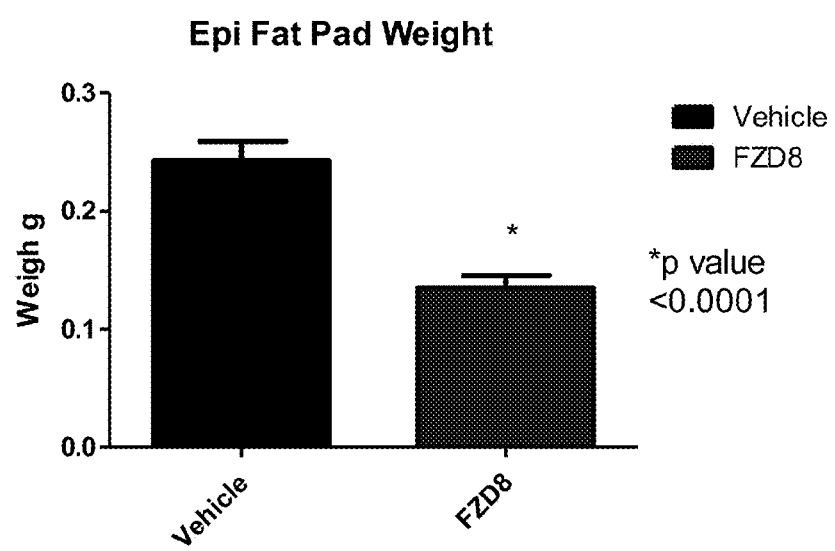
FIG. 9 shows the epididymal fat pad weight of mice fed a regular diet after receiving vehicle or Fzd8 ECD-Fc by hydrodynamic tail vein transfection, as described in Example 3.

FIG. 9 shows epididymal fat pad weight in the mice following necropsy. The epididymal fat pads of the Fzd8 ECD-Fc-treated mice weighed significantly less than the fat pads from vehicle-treated mice.

Example 4

Fzd8 ECD-Fc Administration Prevents Diet-induced Obesity in Rats

Study Procedure

Ten five-week-old male Sprague-Dawley rats (Charles River Labs, Wilmington, Mass.) were administered Fzd8 ECD-Fc and ten five-week-old male Sprague-Dawley rats were administered vehicle (0.9% NaCl) by hydrodynamic tail vein transfection. Each Fzd8 ECD-Fc-treated rat received 500 μg of DNA in 16 ml 0.9% NaCl by hydrodynamic tail vein transfection. Vehicle-treated rats received 16 ml 0.9% NaCl by hydrodynamic tail vein transfection. The rats were switched to a high fat diet after hydrodynamic tail vein transfection.

Following hydrodynamic tail vein transfection, body weight and food consumption were recorded at various time points throughout the study. Food consumption was determined by measuring the remaining weight of food left in the feeder relative to the starting amount.

Results

Figure 10:
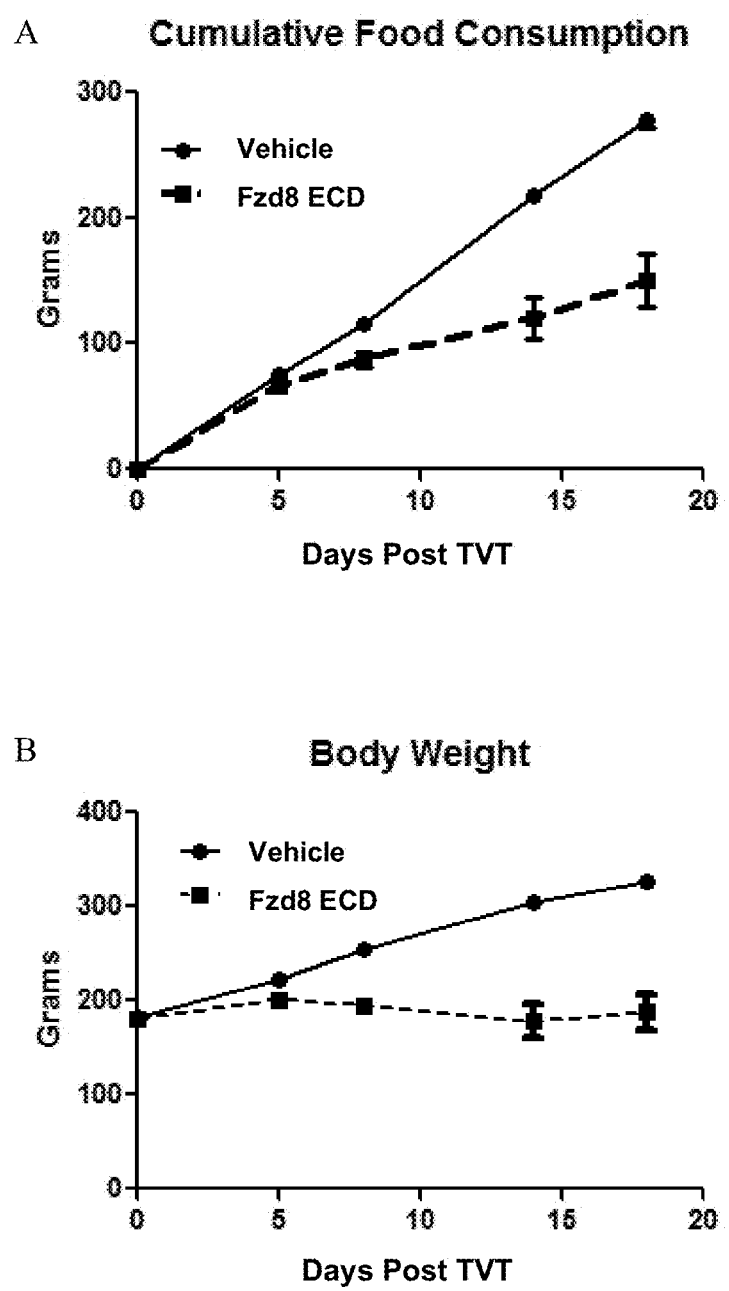
FIG. 10 shows (A) mean cumulative food consumption and (B) mean body weight of rats fed a high fat diet after receiving vehicle or Fzd8 ECD-Fc by hydrodynamic tail vein transfection, as described in Example 4.

FIG. 10 shows the mean cumulative food consumption (A) and mean body weight (B) of the rats over the course of the 18 day study. After 18 days, the mean body weight of vehicle-treated rats was 325 grams, while the mean body weight of Fzd8 ECD-Fc-treated rats was 188 grams, a body weight difference of 43%. After 18 days, the cumulative food consumption was 278 grams for vehicle-treated rats, and 150 grams for Fzd8 ECD-Fc-treated rats, representing a cumulative food consumption difference of 46%.

Example 5

Fzd8 ECD-Fc Administration Causes Weight Loss in Mice

Study Procedure

Ten eight-week-old female C57BL/6 mice (Jackson Labs) were administered Fzd8 ECD-Fc and ten eight-week-old female C57BL/6 mice were administered vehicle (0.9% NaCl) by hydrodynamic tail vein transfection. Each Fzd8 ECD-Fc-treated mouse received 25 μg of DNA in 2 ml 0.9% NaCl by hydrodynamic tail vein transfection. Vehicle-treated mice received 2 ml 0.9% NaCl by hydrodynamic tail vein transfection. After hydrodynamic tail vein transfection, the mice were switched to a high fat diet. Body weights were measured at various time points during the study.

Results

Figure 11:
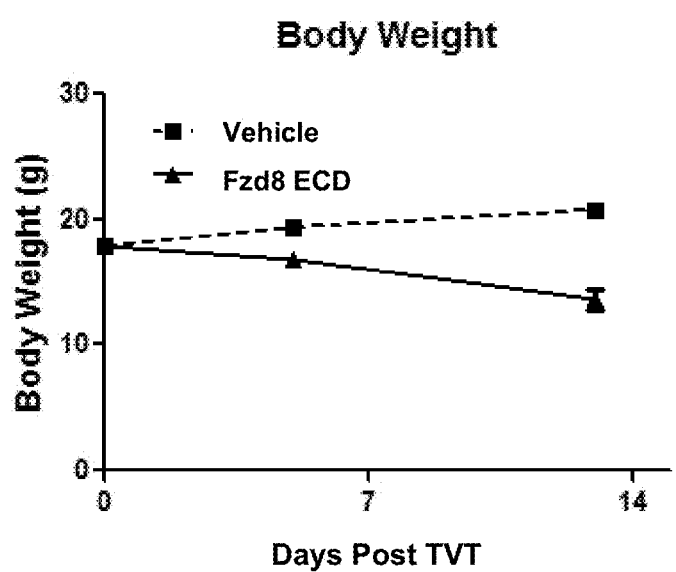
FIG. 11 shows mean body weight of mice fed a high fat diet after receiving vehicle or Fzd8 ECD-Fc by hydrodynamic tail vein transfection, as described in Example 5.

FIG. 11 shows the mean body weight of the mice over the course of the two week study. At the start of the study, the mean body weight for all mice was 17.8 grams. After two weeks, the mean body weight of the Fzd8 ECD-Fc-treated mice was 13.6 grams, representing weight loss of 24%.

Example 6

Fzd8 ECD-Fc Administration Prevents Diet-induced Glucose Intolerance and Hyperglycemia in Mice Study Procedure Ten 13-week-old female C57BL/6 mice (Charles River Labs) were administered Fzd8 ECD-Fc and ten 13-week-old female C57BL/6 mice were administered vehicle (0.9% NaCl) by hydrodynamic tail vein transfection. Each Fzd8 ECD-Fc-treated mouse received 25 μg of DNA in 2 ml 0.9% NaCl by hydrodynamic tail vein transfection. Vehicle-treated mice received 2 ml 0.9% NaCl by hydrodynamic tail vein transfection. The mice were switched to a high fat diet after hydrodynamic tail vein transfection.

Body weight was measured at various time points during the study. Ten weeks after administration of Fzd8 ECD-Fc or vehicle, a glucose tolerance test (GTT) was conducted after a four hour fast. Blood glucose levels were measured with a glucometer from a blood drop at the tip of the tail after the four hour fast, and then at 30 minute intervals after a bolus intraperitoneal dose of 4.0 g/kg glucose.

Results

Figure 12:
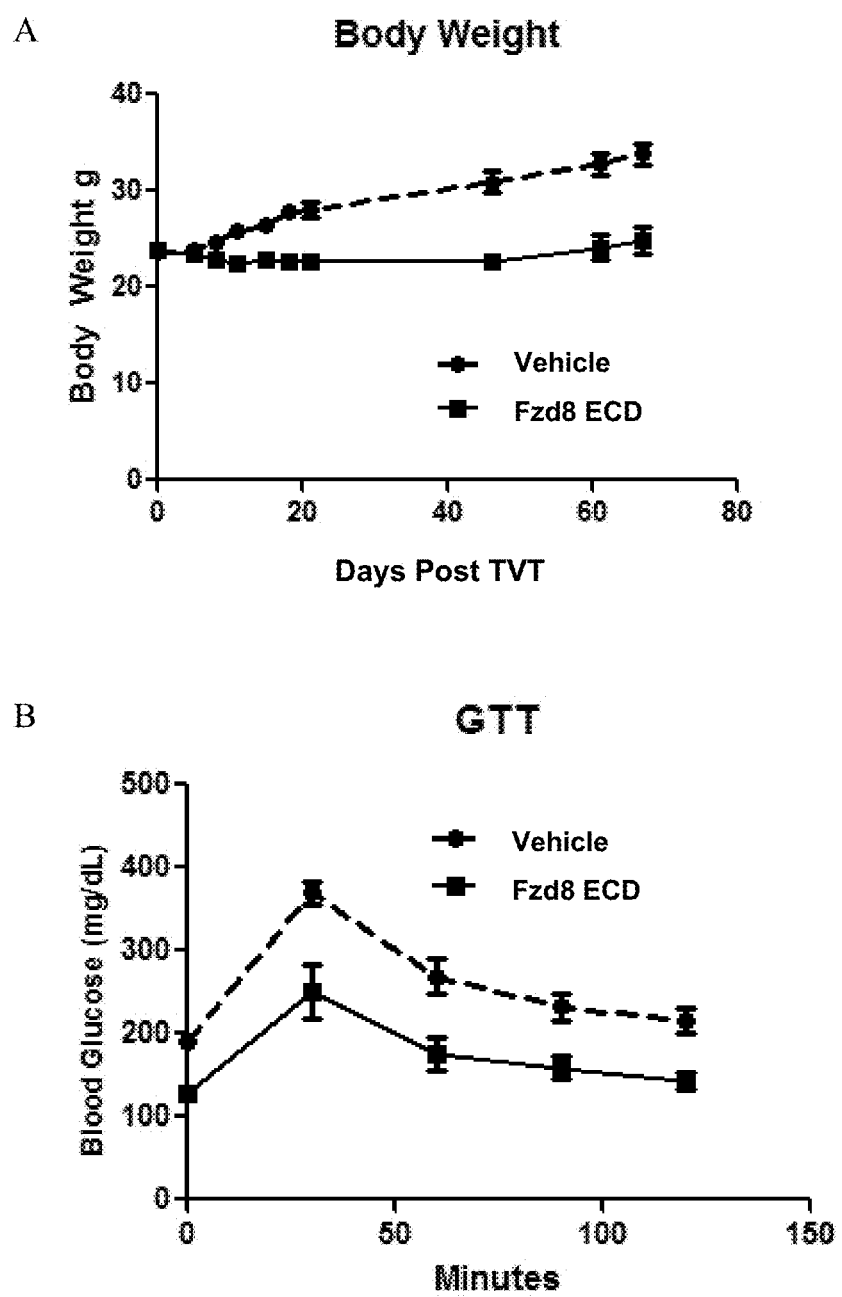
FIG. 12 shows (A) mean body weight and (B) glucose tolerance of mice fed a high fat diet after receiving vehicle or Fzd8 ECD-Fc by hydrodynamic tail vein transfection, as described in Example 6.

FIG. 12 shows (A) mean body weight over the course of the ten week study and (B) mean glucose tolerance at 10 weeks after Fzd8 ECD-Fc administration. After ten weeks, the mean body weight of the vehicle-treated mice was 34 grams, while the mean body weight of the Fzd8 ECD-Fc-treated mice was 25 grams, a difference of 36%. Fasting blood glucose was 33% lower in Fzd8 ECD-Fc-treated mice compared to vehicle treated mice. Additionally, blood glucose levels at all time points after glucose administration were 32%-35% lower in Fzd8 ECD-Fc-treated mice relative to vehicle treated mice.

Example 7

Figure 13:
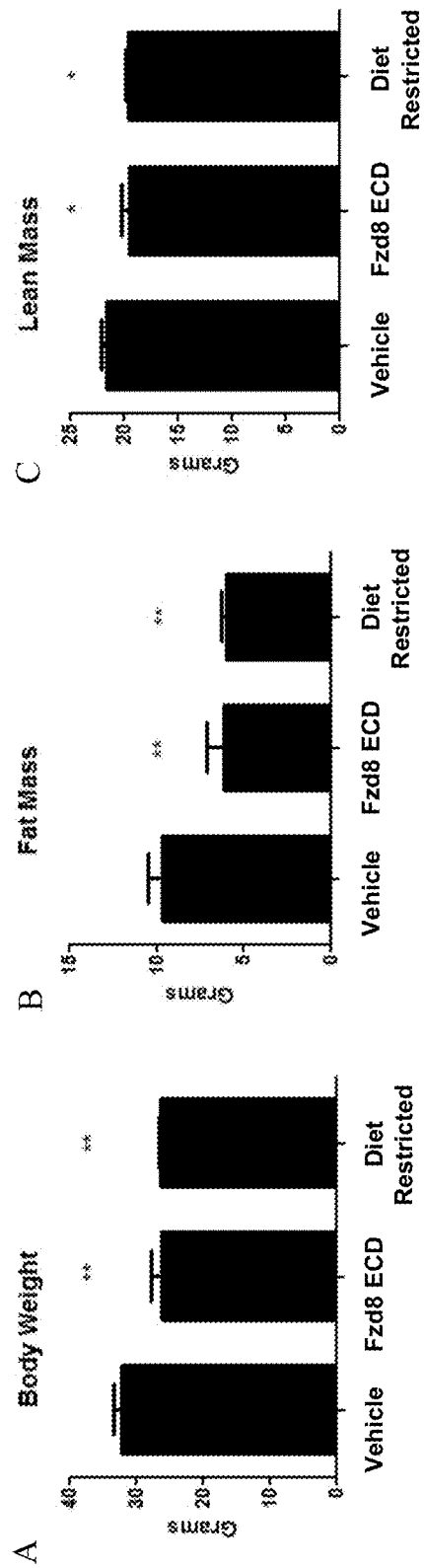
FIG. 13 shows (A) mean body weight, (b) mean fat mass, and (C) mean lean mass of mice fed a high fat diet after receiving Fzd8 ECD-Fc by hydrodynamic tail vein transfection, and of mice fed either a high fat diet or a high-fat restricted diet after receiving vehicle by hydrodynamic tail vein transfection, as described in Example 7.

Fzd8 ECD-Fc Administration Leads to a Body Mass Composition That is Equivalent to the Body Mass Composition in Dieting Mice Study Procedure Ten eight-week-old male C57BL/6 mice (Charles River Labs) were administered Fzd8 ECD-Fc and ten eight-week-old male C57BL/6 mice were administered vehicle (0.9% NaCl) by hydrodynamic tail vein transfection. Each Fzd8 ECD-Fc-treated mouse received 25 μg of DNA in 2 ml 0.9% NaCl by hydrodynamic tail vein transfection. Vehicle-treated mice received 2 ml 0.9% NaCl by hydrodynamic tail vein transfection. After hydrodynamic tail vein transfection, the mice were maintained on a high fat diet, and the vehicle-treated mice were divided into two groups, one of which was diet-restricted, being fed 1.7 grams of food per day. The other vehicle-treated group had an average food consumption of 2.2 grams per day. Body weight and qNMR body mass composition analysis were conducted on day 22 using an EchoMRI-700™ with mouse attachment (Echo Medical Systems, Houston, Tex.).
Results FIG. 13 shows (A) mean body weight, (B) mean fat mass, and (C) mean lean mass of vehicle-treated, Fzd8 ECD-Fc-treated, and diet-restricted mice on day 22. The mean body weight of vehicle-treated, Fzd8 ECD-Fc-treated, and diet-restricted mice was 32 grams, 26 grams, and 26 grams, respectively. The mean fat mass of vehicle-treated, Fzd8 ECD-Fc-treated, and diet-restricted mice was 9.7 grams, 6.2 grams and 6.0 grams, respectively. Finally, the mean lean mass of vehicle-treated, Fzd8 ECD-Fc-treated, and diet-restricted mice was 21.7 grams, 19.5 grams, and 19.6 grams, respectively. The mean body weight, mean lean mass, and mean fat mass were indistinguishable between Fzd8 ECD-Fc-treated and diet-restricted mice in this experiment.

Example 8

Recombinant Human Fzd8 ECD-Fc Administration Prevents Obesity in Mice

Production of Recombinant Human Fzd8 ECD-Fc

A pTT5 vector that expresses human Fzd8 ECD.155-Fc (SEQ ID NO: 5) was transiently transfected into CHO cells and the cells were grown in a shaker flask for 6 days in CD DG44 medium (Gibco/Invitrogen, Carlsbad, Calif.)+8 mM glutamine+0.18% Pluronic® F-68 polyol (Mediatech, Manassas, Va.). Cells were pelleted by centrifugation at 5000×g. The supernatant was loaded directly onto a 30 ml MabSelect SuRe protein A purification column (GE Healthcare, Waukesha, Wis.) equilibrated in 1×PBS with 500 mM NaCl ("Buffer A"). The column was washed with Buffer A and the rhFzd8 ECD-Fc was eluted using a linear gradient to Buffer B (0.1 M glycine, pH 2.7, with 500 mM NaCl) over 20 column volumes. The eluent was collected into 1/10 fraction volume of 1M Tris, pH 8.

Figure 14:
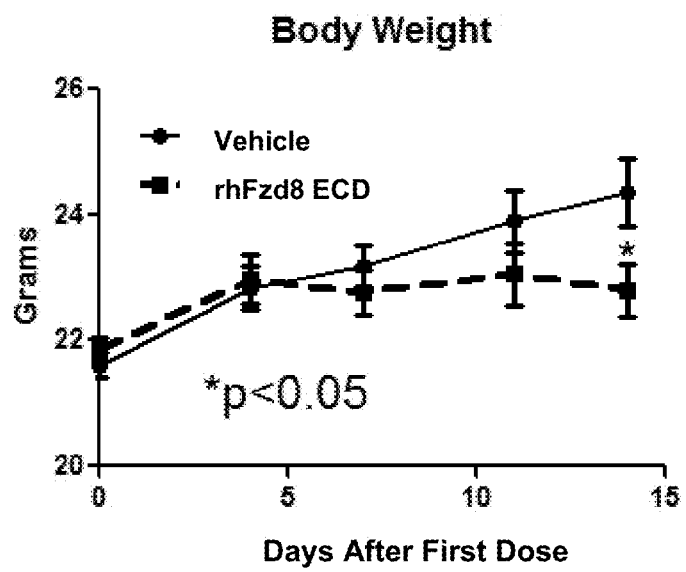
FIG. 14 shows mean body weight of mice fed a high fat diet after administration of rhFzd8 ECD-Fc or vehicle, as described in Example 8.

The pool of fractions from the protein A column containing rhFzd8 ECD-Fc was diluted by addition of 0.8 volumes of 1.6M ammonium sulfate, and loaded onto a 25 ml (1.6×12 cm) butyl sepharose HP column (GE Healthcare) equilibrated in 10 mM potassium phosphate, pH 7, with 0.8 M ammonium sulfate ("Buffer C"). The column was then washed with Buffer C and the rhFzd8 ECD-Fc was eluted using a linear gradient to 10 mM potassium phosphate, pH 7 ("Buffer D") over 15 column volumes. The pool of fractions from the butyl HP column containing rhFzd8 ECD-Fc was dialyzed against 1×PBS, and then concentrated using a spin filter with a 10 kD molecular weight cutoff membrane at 3500×g in a swinging bucket rotor at 4° C.
Study Procedure Eight C57BL/6 mice (Charles River Labs) were administered 10 mg/kg rhFzd8 ECD-Fc in a volume of 0.33 ml 0.9% NaCl on days 0, 4, 8, and 12, and eight mice were administered 0.33 ml 0.9% NaCl on days 0, 4, 8, and 12. Twenty-four hours after the first dose, mice were switched to a high-fat diet. Body weight measurements were taken at various time points during the study.
Results FIG. 14 shows mean body weight of rhFzd8 ECD-Fc-treated and vehicle-treated mice. At the beginning of the study, the mean body weight of all of the mice was 21.7 grams. After 14 days, the mean body weight of rhFzd8 ECD-Fc-administered and vehicle-administered mice was 22.8 grams and 24.4 grams, respectively. The difference in mean body weight between the two groups was statistically significant, with p<0.05.

Example 9

Fzd8 ECD-Fc Administration Leads to a Decrease in NPY Expression in the Hypothalamus of Mice Study Procedure Ten eight-week-old male C57BL/6 mice (Charles River Labs) were administered Fzd8 ECD-Fc and ten mice were administered human IgG1 C237S Fc alone by hydrodynamic tail vein transfection. Each mouse received 20 µg of DNA in 2 ml of Ringer's solution by hydrodynamic tail vein transfection.

Mice were switched to a high fat diet after hydrodynamic tail vein transfection. Body weight was measured at certain time points throughout the study. Mice were bled on day 5 for measuring plasma protein expression in order to determine transfection efficiency. At 21 days after transfection, mice were euthanized by isoflurane and decapitation and the hypothalamus removed and flash-frozen in liquid nitrogen.

Figure 15:
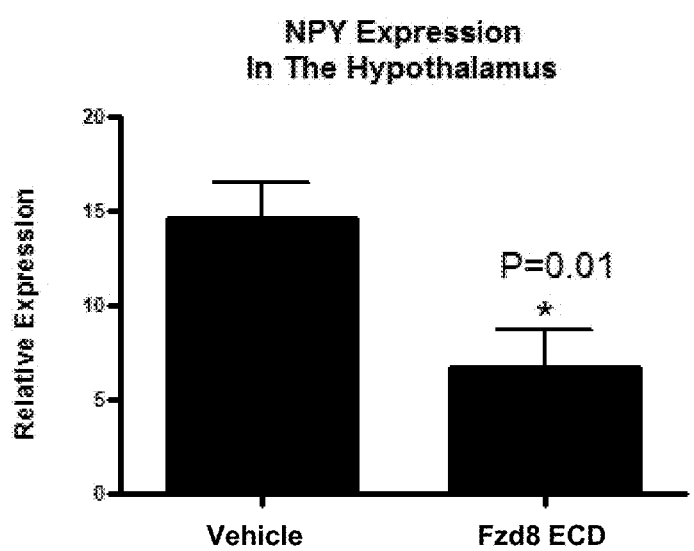
FIG. 15 shows NPY expression in the hypothalamus of mice fed a high fat diet after receiving Fc or Fzd8 ECD-Fc by hydrodynamic tail vein transfection, as described in Example 9.

NPY is a neuropeptide that has been shown to correlate with appetite and food consumption. NPY mRNA expression in the hypothalamus increases during fasting and exogenous administration of NPY will lead to increased food consumption. NPY expression in the hypothalamus was measured by qRT-PCR using a QuantiTect Primer Assay (Qiagen, Valencia, Calif.), and normalized to β-glucuronidase (GUSB).
Results FIG. 15 shows mean NPY expression in the hypothalamus of Fc-treated mice and Fzd8 ECD-Fc-treated mice. NPY expression in Fzd8 ECD-Fc-treated mice was about 50% lower than NPY expression in Fc-treated mice.

Example 10

Fzd8 ECD-Fc, but not Fzd5 ECD-Fc, Prevents Diet-induced Obesity in Mice

Study Procedure

Ten eight-week-old male C57BL/6 mice (Charles River Labs) were administered Fzd8 ECD-Fc, Ten mice were administered Fzd5 ECD-Fc, and ten mice were administered human IgG1 C237S Fc alone by hydrodynamic tail vein transfection. Each mouse received 20 µg of DNA in 2 ml of Ringer's solution by hydrodynamic tail vein transfection.

Figure 16:
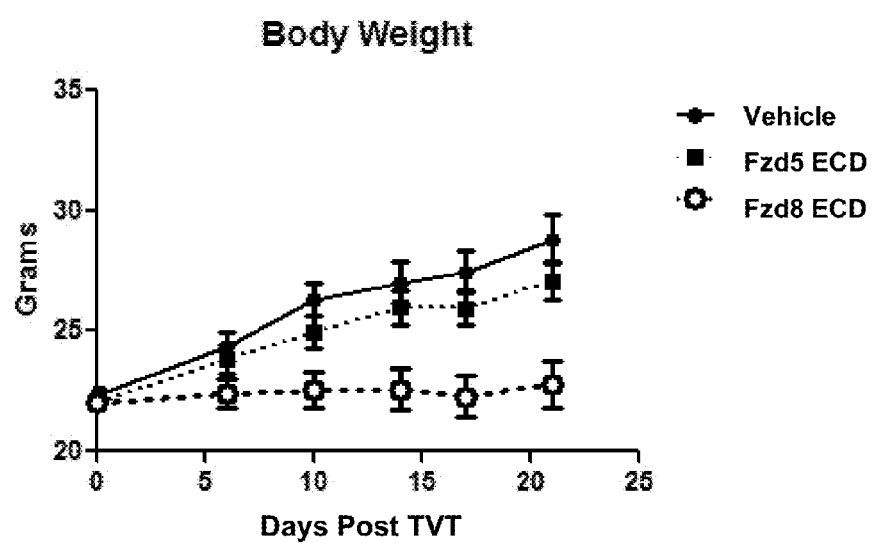
FIG. 16 shows mean body weight of mice fed a high fat diet after receiving Fc, Fzd8 ECD-Fc, or Fzd5 ECD-Fc by hydrodynamic tail vein transfection, as described in Example 10.

Mice were switched to a high fat diet after hydrodynamic tail vein transfection. Body weight and food consumption were recorded twice per week throughout the 21-day study. Mice were bled on day 5 for measuring plasma protein expression in order to determine transfection efficiency. Fzd8 ECD-Fc was found to be present at average 876 µg/ml and Fzd5 ECD-Fc was found to be present at an average of 294 µg/ml.
Results FIG. 16 shows the mean body weight of Fzd8 ECD-Fc-treated mice, Fzd5 ECD-Fc-treated mice, and Fc-treated mice throughout the study. Both the Fzd5 ECD-Fc-treated and the Fc-treated mice gained significant weight during the study, while the Fzd8 ECD-Fc-treated mice gained little or no weight during the course of the study.

Although the foregoing invention has been described in some detail by way of illustration and example for purposes of clarity of understanding, the descriptions and examples should not be construed as limiting the scope of the invention. The disclosures of all patent and scientific literatures cited herein are expressly incorporated in their entirety by reference.

Table of Sequences

Table 3 lists certain sequences discussed herein. Fzd8 sequences are shown without the signal peptide, unless otherwise indicated.

TABLE 3

Sequences and Descriptions

| SEQ ID NO | Description | Sequence |
|---|---|---|
| 1 | Human Fdz8 (with signal peptide) | MEWGYLLEVT SLLAALALLQ RSSGAAAASA KELACQEITV PLCKGIGYNY TYMPNQFNHD TQDEAGLEVH QFWPLVEIQC SPDLKFFLCS MYTPICLEDY KKPLPPCRSV CERAKAGCAP LMRQYGFAWP DRMRCFRLPE QGNPDTLCMD YNRTDLTTAA PSPPRRLPPP PPGEQPPSGS GHGRPPGARP PHRGGGRGGG GGDAAAPPAR GGGGGGKARP PGGGAAPCEP GCQCRAPMVS VSSERHPLYN RVKTGQIANC ALPCHNPFFS QDERAFTVFW IGLWSVLCFV STFATVSTFL IDMERFKYPE RPIIFLSACY LFVSVGYLVR LVAGHEKVAC SGGAPGAGGA GGAGGAAAGA GAAGAGAGGP GGRGEYEELG AVEQHVRYET TGPALCTVVF LLVYFFGMAS SIWWVILSLT WFLAAGMKWG NEAIAGYSQY FHLAAWLVPS VKSIAVLALS SVDGDPVAGI CYVGNQSLDN LRGFVLAPLV IYLFIGTMFL LAFGVSLFRI RSVIKQQDGP TKTHKLEKLM IRLGLFTVLY TVPAAVVVAC LFYEQHNRPR WEATHNCPCL RDLQPDQARR PDYAVFMLKY FMCLVVGITS GVWVWSGKTL ESWRSLCTRC CWASKGAAVG GGAGATAAGG GGGPGGGGGG GPGGGGPGG GGGSLYSDVS TGLTWRSGTA SSVSYPKQMP LSQV |
| 2 | Human Fzd8 (without signal peptide) | ASA KELACQEITV PLCKGIGYNY TYMPNQFNHD TQDEAGLEVH QFWPLVEIQC SPDLKFFLCS MYTPICLEDY KKPLPPCRSV CERAKAGCAP LMRQYGFAWP DRMRCDRLPE QGNPDTLCMD YNRTDLTTAA PSPPRRLPPP PPGEQPPSGS GHGRPPGARP PHRGGGRGGG GGDAAAPPAR GGGGGGKARP PGGGAAPCEP GCQCRAPMVS VSSERHPLYN RVKTGQIANC ALPCHNPFFS QDERAFTVFW IGLWSVLCFV STFATVSTFL IDMERFKYPE RPIIFLSACY LFVSVGYLVR LVAGHEKVAC SGGAPGAGGA GGAGGAAAGA GAAGAGAGGP GGRGEYEELG AVEQHVRYET TGPALCTVVF LLVYFFGMAS SIWWVILSLT WFLAAGMKWG NEAIAGYSQY FHLAAWLVPS VKSIAVLALS SVDGDPVAGI CYVGNQSLDN LRGFVLAPLV IYLFIGTMFL LAFGVSLFRI RSVIKQQDGP TKTHKLEKLM IRLGLFTVLY TVPAAVVVAC LFYEQHNRPR WEATHNCPCL RDLQPDQARR PDYAVFMLKY FMCLVVGITS GVWVWSGKTL ESWRSLCTRC CWASKGAAVG GGAGATAAGG GGGPGGGGGG GPGGGGPGG GGGSLYSDVS TGLTWRSGTA SSVSYPKQMP LSQV |
| 3 | Full-length human Fzd8 ECD (with signal peptide); Sp-hFzd8-ECD.275 | MEWGYLLEVTSLLAALALLQRSSGAAAASAKELACQEITVPLCK GIGYNYTYMPNQFNHDTQDEAGLEVHQFWPLVEIQCSPDLKFFL CSMYTPICLEDYKKPLPPCRSVCERAKAGCAPLMRQYGFAWPDR MRCDRLPEQGNPDTLCMDYNRTDLTTAAPSPPRRLPPPPPGEQP PSGSGHGRPPGARPPHRGGGRGGGGDAAAPPARGGGGGGKARP PGGGAAPCEPGCQCRAPMVSVSSERHPLYNRVKTGQIANCALPC HNPFFSQDERA |
| 4 | Full-length human Fzd8 ECD (without signal peptide); hFzd8-ECD.275 | ASAKELACQEITVPLCKGIGYNYTYMPNQFNHDTQDEAGLEVHQ FWPLVEIQCSPDLKFFLCSMYTPICLEDYKKPLPPCRSVCERAK AGCAPLMRQYGFAWPDRMRCDRLPEQGNPDTLCMDYNRTDLTTA APSPPRRLPPPPPGEQPPSGSGHGRPPGARPPHRGGGRGGGGD AAAPPARGGGGGKARPPGGGAAPCEPGCQCRAPMVSVSSERHP LYNRVKTGQIANCALPCHNPFFSQDERA |
| 12 | hFzd8-ECD.155 | ASAKELACQE ITVPLCKGIG YNYTYMPNQF NHDTQDEAGL EVHQFWPLVE IQCSPDLKFF LCSMYTPICL EDYKKPLPPC RSVCERAKAG CAPLMRQYGF AWPDRMRCDR LPEQGNPDTL CMDYNRTD |
| 13 | SP-hFzd8-ECD.155 | MEWGYLLEVT SLLAALALLQ RSSGAAAASA KELACQEITV PLCKGIGYNY TYMPNQFNHD TQDEAGLEVH QFWPLVEIQC SPDLKFFLCS MYTPICLEDY KKPLPPCRSV CERAKAGCAP LMRQYGFAWP DRMRCDRLPE QGNPDTLCMD YNRTD |
| 14 | hFzd8-ECD.275-Fc | MEWGYLLEVTSLLAALALLQRSSGAAAASAKELACQEITVPLCK GIGYNYTYMPNQFNHDTQDEAGLEVHQFWPLVEIQCSPDLKFFL CSMYTPICLEDYKKPLPPCRSVCERAKAGCAPLMRQYGFAWPDR MRCDRLPEQGNPDTLCMDYNRTDLTTAAPSPPRRLPPPPPGEQP PSGSGHGRPPGARPPHRGGGRGGGGDAAAPPARGGGGGGKARP PGGGAAPCEPGCQCRAPMVSVSSERHPLYNRVKTGQIANCALPC HNPFFSQDERAGSEPKSSDKT HTCPPCPAPE LLGGPSVFLF |

TABLE 3-continued

Sequences and Descriptions

| SEQ ID NO | Description | Sequence |
|---|---|---|
| | | PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV LTCLVKGFYP SDIAVEWESN GQPENNYKTT PPVLDSDGSF FLYSKLTVDK SRWQQGNVFS CSVMHEALHN HYTQKSLSLS PGK |
| 15 | SP-hFzd8-ECD.275-Fc | ASAKELACQEITVPLCKGIGYNYTYMPNQFNHDTQDEAGLEVHQ FWPLVEIQCSPDLKFFLCSMYTPICLEDYKKPLPPCRSVCERAK AGCAPLMRQYGFAWPDRMRCDRLPEQGNPDTLCMDYNRTDLTTA APSPPRRLPPPPPGEQPPSGSGHGRPPGARPPHRGGGRGGGGGD AAAPPARGGGGGGKARPPGGGAAPCEPGCQCRAPMVSVSSERHP LYNRVKTGQIANCALPCHNPFFSQDERAGSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV LTCLVKGFYP SDIAVEWESN GQPENNYKTT PPVLDSDGSF FLYSKLTVDK SRWQQGNVFS CSVMHEALHN HYTQKSLSLS PGK |
| 5 | hFzd8-ECD.155-Fc with GS linker | ASAKELACQEITVPLCKGIGYNYTYMPNQFNHDTQDEAGLEVHQ FWPLVEIQCSPDLKFFLCSMYTPICLEDYKKPLPPCRSVCERAK AGCAPLMRQYGFAWPDRMRCDRLPEQGNPDTLCMDYNRTDGSEP KSSDKTHTCPPCPAPELLGGPSVFLFPPKPKDTLMISRTPEVTC VVVDVSHEDPEVKFNWYVDGVEVHNAKTKPREEQYNSTYRVVSV LTVLHQDWLNGKEYKCKVSNKALPAPIEKTISKAKGQPREPQVY TLPPSRDELTKNQVSLTCLVKGFYPSDIAVEWESNGQPENNYKT TPPVLDSDGSFFLYSKLTVDKSRWQQGNVFSCSVMHEALHNHYT QKSLSLSPGK |
| 6 | SP-hFzd8-ECD.155-Fc with GS linker | MEWGYLLEVTSLLAALALLQRSSGAAAASAKELACQEITVPLCK GIGYNYTYMPNQFNHDTQDEAGLEVHQFWPLVEIQCSPDLKFFL CSMYTPICLEDYKKPLPPCRSVCERAKAGCAPLMRQYGFAWPDR MRCDRLPEQGNPDTLCMDYNRTDGSEPKSSDKTHTCPPCPAPEL LGGPSVFLFPPKPKDTLMISRTPEVTCVVVDVSHEDPEVKFNWY VDGVEVHNAKTKPREEQYNSTYRVVSVLTVLHQDWLNGKEYKCK VSNKALPAPIEKTISKAKGQPREPQVYTLPPSRDELTKNQVSLT CLVKGFYPSDIAVEWESNGQPENNYKTTPPVLDSDGSFFLYSKL TVDKSRWQQGNVFSCSVMHEALHNHYTQKSLSLSPGK |
| 7 | hFzd8 signal peptide | MEWGYLLEVTSLLAALALLQRSSGAAA |
| 8 | Fc C237S | EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 9 | Exemplary Fc #1 | ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 10 | Exemplary Fc #2 | ESKYGPPCPS CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 11 | Fc C237S with N-terminal GS linker | GSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV LTCLVKGFYP SDIAVEWESN GQPENNYKTT PPVLDSDGSF FLYSKLTVDK SRWQQGNVFS CSVMHEALHN HYTQKSLSLS PGK |
| 16 | Fzd5 ECD-Fc | MARPDPSAPP SLLLLLLAQL VGRAAASKA PVCQEITVPM CRGIGYNLTH MPNQFNHDTQ DEAGLEVHQF WPLVEIQCSP DLRFFLCSMY TPICLPDYHK PLPPCRSVCE RAKAGCSPLM RQYGFAWPER MSCDRLPVLG RDAEVLCMDY NRSEGPAEPK SSDKTHTCPP CPAPELLGGP SVFLFPPKPK DTLMISRTPE VTCVVVDVSH EDPEVKFNWY VDGVEVHNAK TKPREEQYNS |

TABLE 3-continued

Sequences and Descriptions

| SEQ ID NO | Description | Sequence |
|---|---|---|
| | | TYRVVSVLTV LHQDWLNGKE YKCKVSNKAL PAPIEKTISK AKGQPREPQV YTLPPSRDEL TKNQVSLTCL VKGFYPSDIA VEWESNGQPE NNYKTTPPVL DSDGSFFLYS KLTVDKSRWQ QGNVFSCSVM HEALHNHYTQ KSLSLSPGK |
| 17 | hFzd8-ECD.155-Fc without GS linker | ASAKELACQEITVPLCKGIGYNYTYMPNQFNHDTQDEAGLEVHQ FWPLVEIQCSPDLKFFLCSMYTPICLEDYKKPLPPCRSVCERAK AGCAPLMRQYGFAWPDRMRCDRLPEQGNPDTLCMDYNRTDEPKS SDKTHTCPPCPAPELLGGPSVFLFPPKPKDTLMISRTPEVTCVV VDVSHEDPEVKFNWYVDGVEVHNAKTKPREEQYNSTYRVVSVLT VLHQDWLNGKEYKCKVSNKALPAPIEKTISKAKGQPREPQVYTL PPSRDELTKNQVSLTCLVKGFYPSDIAVEWESNGQPENNYKTTP PVLDSDGSFFLYSKLTVDKSRWQQGNVFSCSVMHEALHNHYTQK SLSLSPGK |
| 18 | SP-hFzd8-ECD.155-Fc without GS linker | MEWGYLLEVTSLLAALALLQRSSGAAAASAKELACQEITVPLCK GIGYNYTYMPNQFNHDTQDEAGLEVHQFWPLVEIQCSPDLKFFL CSMYTPICLEDYKKPLPPCRSVCERAKAGCAPLMRQYGFAWPDR MRCDRLPEQGNPDTLCMDYNRTDEPKSSDKTHTCPPCPAPELLG GPSVFLFPPKPKDTLMISRTPEVTCVVVDVSHEDPEVKFNWYVD GVEVHNAKTKPREEQYNSTYRVVSVLTVLHQDWLNGKEYKCKVS NKALPAPIEKTISKAKGQPREPQVYTLPPSRDELTKNQVSLTCL VKGFYPSDIAVEWESNGQPENNYKTTPPVLDSDGSFFLYSKLTV DKSRWQQGNVFSCSVMHEALHNHYTQKSLSLSPGK |

The invention claimed is:

1. A method of lowering free fatty acid levels in a subject with high free fatty acid levels comprising administering to the subject an effective amount of a frizzled-8 (Fzd8) extracellular domain (ECD) or the Fzd8 ECD fusion molecule comprising a Fzd8 ECD and at least one fusion partner, wherein the Fzd8 ECD comprises the sequence of SEQ ID NO: 12 or a sequence that is 95% identical to the sequence of SEQ ID NO: 12.

2. A method of lowering a blood glucose level in a subject with a high blood glucose level comprising administering to the subject an effective amount of a frizzled-8 (Fzd8) extracellular domain (ECD) or a Fzd8 ECD fusion molecule comprising the Fzd8 ECD and at least one fusion partner, wherein the Fzd8 ECD comprises the sequence of SEQ ID NO: 12 or a sequence that is 95% identical to the sequence of SEQ ID NO: 12.

3. A method of reducing NPY expression in the hypothalamus of a subject in need of reduced NPY expression, comprising administering to the subject an effective amount of a frizzled-8 (Fzd8) extracellular domain (ECD) or the Fzd8 ECD fusion molecule comprising a Fzd8 ECD and at least one fusion partner, wherein the Fzd8 ECD comprises the sequence of SEQ ID NO: 12 or a sequence that is 95% identical to the sequence of SEQ ID NO: 12.

4. The method of any one of claims 1, 2, and 3, wherein the Fzd8 ECD has the sequence of SEQ ID NO.: 3, 4, 12, or 13.

5. The method of any one of claims 1, 2, and 3, wherein at least one fusion partner is selected from an Fc, albumin, and polyethylene glycol.

6. The method of claim 5, wherein at least one fusion partner is an Fc.

7. The method of any one of claims 1, 2, and 3, wherein the fusion molecule comprises a linker between the Fzd8 ECD and one or more fusion partners.

8. The method of any one of claims 1, 2, and 3, wherein the Fzd8 ECD fusion molecule comprises the amino acid sequence of SEQ ID NO.: 5, 6, 14, 15, 17, or 18.

9. The method of claim 8, wherein the Fzd8 ECD fusion molecule consists of the amino acid sequence of SEQ ID NO.: 5, 6, 14, 15, 17, or 18.

10. The method of any one of claims 1, 2, and 3, wherein the Fzd8 ECD comprises the sequence of SEQ ID NO: 4 or a sequence that is 95% identical to the sequence of SEQ ID NO: 4.

11. The method of any one of claims 1, 2, and 3, wherein the method further comprises administering a therapeutic agent selected from phentermine, orlistat, sibutramin HCl monohydrate, lorcaserin, phentermine/topiramate, naltrexone SR/bupropion SR, liraglutide, cetilistat, pramlintide/metreleptin, betahistine, zonisamide SR/bupropion SR, tesofensine, velneperit, davalintide, and obinepitide.

* * * * *

UNITED STATES PATENT AND TRADEMARK OFFICE
CERTIFICATE OF CORRECTION

PATENT NO. : 8,431,532 B2
APPLICATION NO. : 13/169900
DATED : April 30, 2013
INVENTOR(S) : Thomas Brennan, Ernestine Lee and Steven Smith It is certified that error appears in the above-identified patent and that said Letters Patent is hereby corrected as shown below:

Title Page, item (73) Assignee should read:
--Five Prime Therapeutics, Inc., South San Francisco, CA (US)--

Signed and Sealed this
Eleventh Day of June, 2013

Teresa Stanek Rea
*Acting Director of the United States Patent and Trademark Office*